(12) United States Patent  (10) Patent No.: US 7,875,028 B2
Christian et al.  (45) Date of Patent: Jan. 25, 2011

(54) ABLATION DEVICE WITH JAWS

(75) Inventors: Steven C. Christian, Brooklyn Park, MN (US); Paul T. Rothstein, Elk River, MN (US); Tom P. Daigle, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/499,356

(22) Filed: Jul. 8, 2009

(65) Prior Publication Data

US 2009/0270857 A1  Oct. 29, 2009

Related U.S. Application Data

(62) Division of application No. 11/142,954, filed on Jun. 2, 2005, now Pat. No. 7,566,334.

(60) Provisional application No. 60/576,096, filed on Jun. 2, 2004, provisional application No. 60/581,139, filed on Jun. 18, 2004.

(51) Int. Cl.
*A61B 18/18* (2006.01)
(52) U.S. Cl. .............................. 606/51; 606/52; 606/49; 606/41; 606/205
(58) Field of Classification Search ............. 606/50–52, 606/205–207
See application file for complete search history.

(56) References Cited

U.S. PATENT DOCUMENTS 1,127,948 A  2/1915  Wappler (Continued)

FOREIGN PATENT DOCUMENTS

DE  43 13 903  9/1994

(Continued)

OTHER PUBLICATIONS

Ki-Bong Kim, M.D., et al., Abstract "The Cox-Maze III Procedure for Atrial Fibrillation Associated with Rheumatic Mitral Valve Disease," The Annals of Thoracic Surgery, 2000; pp. 1-5.

(Continued)

*Primary Examiner*—Thomas J Sweet
*Assistant Examiner*—Amanda Scott
(74) *Attorney, Agent, or Firm*—Mike Jaro; Jeffrey J. Hohenshell

(57) ABSTRACT

System, device and method for ablating target tissue adjacent pulmonary veins of a patient through an incision. An ablation device can include a hinge including a cam assembly, a moving arm, a floating jaw, and a lower jaw. Fingers can engage the floating jaw to hold the floating jaw in a first position with respect to the moving arm. Some embodiments of the invention can provide an ablation device including a central support, an upper four-bar linkage coupled to the central support, an upper jaw coupled to the upper linkage, a lower four-bar linkage coupled to the central support, and a lower jaw coupled to the lower linkage. Some embodiments of the invention can provide an ablation device having an upper jaw including a first cannula connection and a lower jaw including a second cannula connection. The system can include a first catheter coupled to the first cannula connection and a second catheter coupled to the second cannula connection. The first and second catheters can be inserted through the incision and can move the upper and lower jaws adjacent the pulmonary veins.

6 Claims, 20 Drawing Sheets

U.S. PATENT DOCUMENTS

| | | |
|---|---|---|
| 2,004,559 A | 6/1935 | Wappler et al. |
| 3,470,975 A | 10/1969 | Johnson et al. |
| 3,630,207 A | 12/1971 | Kahn et al. |
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,901,242 A | 8/1975 | Storz |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,043,342 A | 8/1977 | Morrison, Jr. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,312,337 A | 1/1982 | Donohue et al. |
| 4,353,371 A | 10/1982 | Cosman |
| 4,377,168 A | 3/1983 | Rzasa et al. |
| 4,492,231 A | 1/1985 | Auth |
| 4,519,389 A | 5/1985 | Gudkin et al. |
| 4,590,934 A | 5/1986 | Malis et al. |
| 4,598,698 A | 7/1986 | Siegmund |
| 4,601,290 A | 7/1986 | Effron et al. |
| 4,664,110 A | 5/1987 | Schanzlin |
| 4,706,667 A | 11/1987 | Roos |
| 4,732,149 A | 3/1988 | Sutter |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,940,064 A | 7/1990 | Desai |
| 4,946,460 A | 8/1990 | Merry et al. |
| 5,009,661 A | 4/1991 | Michelson |
| 5,013,312 A | 5/1991 | Parins et al. |
| 5,029,574 A | 7/1991 | Shimamura et al. |
| 5,033,477 A | 7/1991 | Chin et al. |
| 5,044,165 A | 9/1991 | Linner et al. |
| 5,044,947 A | 9/1991 | Sachdeva et al. |
| 5,071,428 A | 12/1991 | Chin et al. |
| 5,078,713 A | 1/1992 | Varney |
| 5,080,102 A | 1/1992 | Dory |
| 5,080,660 A | 1/1992 | Buelina |
| 5,083,565 A | 1/1992 | Parins |
| 5,085,657 A | 2/1992 | Ben-Simhon |
| 5,087,243 A | 2/1992 | Avitall |
| 5,100,388 A | 3/1992 | Behl et al. |
| 5,108,390 A | 4/1992 | Potocky et al. |
| 5,116,332 A | 5/1992 | Lottick |
| 5,125,928 A | 6/1992 | Parins et al. |
| 5,147,355 A | 9/1992 | Friedman et al. |
| 5,178,133 A | 1/1993 | Pena |
| 5,190,541 A | 3/1993 | Abele et al. |
| 5,207,674 A | 5/1993 | Hamilton |
| 5,207,691 A | 5/1993 | Nardella |
| 5,217,460 A | 6/1993 | Knoepfler |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,242,441 A | 9/1993 | Avitall |
| 5,242,458 A | 9/1993 | Bendel et al. |
| 5,250,047 A | 10/1993 | Rydell |
| 5,250,075 A | 10/1993 | Badie |
| 5,254,116 A | 10/1993 | Baust et al. |
| 5,254,130 A | 10/1993 | Poncet et al. |
| 5,263,493 A | 11/1993 | Avitall |
| 5,269,291 A | 12/1993 | Carter |
| 5,269,326 A | 12/1993 | Verrier |
| 5,269,780 A | 12/1993 | Roos |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,281,216 A | 1/1994 | Klicek |
| 5,293,869 A | 3/1994 | Edwards et al. |
| 5,295,484 A | 3/1994 | Marcus et al. |
| 5,306,234 A | 4/1994 | Johnson |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,318,589 A | 6/1994 | Lichtman |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,327,905 A | 7/1994 | Avitall |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,354,297 A | 10/1994 | Avitall |
| 5,357,956 A | 10/1994 | Nardella |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,397,339 A | 3/1995 | Desai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,403,312 A | 4/1995 | Yates et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,429,131 A | 7/1995 | Scheinman et al. |
| 5,429,636 A | 7/1995 | Shikhman et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,438,302 A | 8/1995 | Goble |
| 5,441,483 A | 8/1995 | Avitall |
| 5,443,463 A | 8/1995 | Stern et al. |
| 5,443,470 A | 8/1995 | Stern et al. |
| 5,445,638 A | 8/1995 | Rydell et al. |
| 5,449,355 A | 9/1995 | Rhum et al. |
| 5,450,843 A | 9/1995 | Moll et al. |
| 5,451,223 A | 9/1995 | Ben-Simhon |
| 5,452,582 A | 9/1995 | Longsworth |

| | | | | | |
|---|---|---|---|---|---|
| 5,452,733 A | 9/1995 | Sterman et al. | 5,676,692 A | 10/1997 | Sanghvi et al. |
| 5,454,370 A | 10/1995 | Avitall | 5,676,693 A | 10/1997 | Lafontaine |
| 5,462,545 A | 10/1995 | Wang et al. | 5,678,550 A | 10/1997 | Bassen et al. |
| 5,465,716 A | 11/1995 | Avitall | 5,680,860 A | 10/1997 | Imran |
| 5,465,717 A | 11/1995 | Imran et al. | 5,681,278 A | 10/1997 | Igo et al. |
| 5,469,853 A | 11/1995 | Law et al. | 5,681,308 A | 10/1997 | Edwards et al. |
| 5,472,441 A | 12/1995 | Edwards et al. | 5,683,384 A | 11/1997 | Gough et al. |
| 5,472,876 A | 12/1995 | Fahy | 5,687,723 A | 11/1997 | Avitall |
| 5,478,309 A | 12/1995 | Sweezer et al. | 5,687,737 A | 11/1997 | Branham et al. |
| 5,478,330 A | 12/1995 | Imran et al. | 5,688,267 A | 11/1997 | Panescu et al. |
| 5,480,409 A | 1/1996 | Riza | 5,688,270 A | 11/1997 | Yates et al. |
| 5,486,193 A | 1/1996 | Bourne et al. | 5,690,611 A | 11/1997 | Swartz et al. |
| 5,487,385 A | 1/1996 | Avitall | 5,693,051 A | 12/1997 | Schulze et al. |
| 5,487,757 A | 1/1996 | Truckai et al. | 5,697,536 A | 12/1997 | Eggers et al. |
| 5,496,312 A | 3/1996 | Klicek | 5,697,882 A | 12/1997 | Eggers et al. |
| 5,497,774 A | 3/1996 | Swartz et al. | 5,697,925 A | 12/1997 | Taylor |
| 5,498,248 A | 3/1996 | Milder | 5,697,927 A | 12/1997 | Imran et al. |
| 5,500,011 A | 3/1996 | Desai | 5,697,928 A | 12/1997 | Walcott et al. |
| 5,500,012 A | 3/1996 | Brucker et al. | 5,702,359 A | 12/1997 | Hofmann et al. |
| 5,505,730 A | 4/1996 | Edwards | 5,702,390 A | 12/1997 | Austin et al. |
| 5,516,505 A | 5/1996 | McDow | 5,702,438 A | 12/1997 | Avitall |
| 5,520,682 A | 5/1996 | Baust et al. | 5,709,680 A | 1/1998 | Yates et al. |
| 5,522,788 A | 6/1996 | Kuzmak | 5,713,942 A | 2/1998 | Stern |
| 5,522,870 A | 6/1996 | Ben-Zion | 5,716,389 A | 2/1998 | Walinsky et al. |
| 5,531,744 A | 7/1996 | Nardella et al. | 5,718,241 A | 2/1998 | Ben-Haim et al. |
| 5,536,267 A | 7/1996 | Edwards et al. | 5,718,701 A | 2/1998 | Shai et al. |
| 5,545,195 A | 8/1996 | Lennox et al. | 5,718,703 A | 2/1998 | Chin |
| 5,545,200 A | 8/1996 | West et al. | 5,720,775 A | 2/1998 | Lanard |
| 5,549,636 A | 8/1996 | Li | 5,722,402 A | 3/1998 | Swanson et al. |
| 5,549,661 A | 8/1996 | Kordis et al. | 5,722,403 A | 3/1998 | McGee et al. |
| 5,555,883 A | 9/1996 | Avitall | 5,725,512 A | 3/1998 | Swartz et al. |
| 5,558,671 A | 9/1996 | Yates | 5,728,143 A | 3/1998 | Gough et al. |
| 5,560,362 A | 10/1996 | Sliwa, Jr. et al. | 5,730,074 A | 3/1998 | Peter |
| 5,562,699 A | 10/1996 | Heimberger et al. | 5,730,127 A | 3/1998 | Avitall |
| 5,562,700 A | 10/1996 | Huitema et al. | 5,730,704 A | 3/1998 | Avitall |
| 5,562,720 A | 10/1996 | Stern et al. | 5,733,280 A | 3/1998 | Avitall |
| 5,562,721 A | 10/1996 | Marchlinski et al. | 5,735,280 A | 4/1998 | Sherman et al. |
| 5,564,440 A | 10/1996 | Swartz et al. | 5,735,290 A | 4/1998 | Sterman et al. |
| 5,569,241 A | 10/1996 | Edwards | 5,735,847 A | 4/1998 | Gough et al. |
| 5,571,088 A | 11/1996 | Lennox et al. | 5,735,849 A | 4/1998 | Baden et al. |
| 5,571,119 A | 11/1996 | Atala | 5,738,628 A | 4/1998 | Sierocuk et al. |
| 5,571,215 A | 11/1996 | Sterman et al. | 5,740,808 A | 4/1998 | Panescu et al. |
| 5,573,532 A | 11/1996 | Chang et al. | 5,755,664 A | 5/1998 | Rubenstein |
| 5,575,766 A | 11/1996 | Swartz et al. | 5,755,717 A | 5/1998 | Yates et al. |
| 5,575,788 A | 11/1996 | Baker et al. | 5,755,760 A | 5/1998 | Maguire et al. |
| 5,575,805 A | 11/1996 | Li | 5,759,158 A | 6/1998 | Swanson |
| 5,575,810 A | 11/1996 | Swanson et al. | 5,769,846 A | 6/1998 | Edwards et al. |
| 5,578,007 A | 11/1996 | Imran | 5,776,130 A | 7/1998 | Buysse et al. |
| 5,582,609 A | 12/1996 | Swanson et al. | 5,782,827 A | 7/1998 | Gough et al. |
| 5,587,723 A | 12/1996 | Otake et al. | 5,782,828 A | 7/1998 | Chen et al. |
| 5,588,432 A | 12/1996 | Crowley | 5,785,706 A | 7/1998 | Bednarek |
| 5,590,657 A | 1/1997 | Cain et al. | H1745 H | 8/1998 | Paraschac |
| 5,591,192 A | 1/1997 | Privitera et al. | 5,788,636 A | 8/1998 | Curley |
| 5,595,183 A | 1/1997 | Swanson et al. | 5,792,140 A | 8/1998 | Tu et al. |
| 5,599,350 A | 2/1997 | Schulze et al. | 5,797,906 A | 8/1998 | Rhum et al. |
| 5,607,462 A | 3/1997 | Imran | 5,797,959 A | 8/1998 | Castro et al. |
| 5,611,813 A | 3/1997 | Lichtman | 5,797,960 A | 8/1998 | Stevens et al. |
| 5,617,854 A | 4/1997 | Munsif | 5,800,428 A | 9/1998 | Nelson et al. |
| 5,620,459 A | 4/1997 | Lichtman | 5,800,482 A | 9/1998 | Pomeranz et al. |
| 5,630,837 A | 5/1997 | Crowley | 5,800,484 A | 9/1998 | Gough et al. |
| 5,632,717 A | 5/1997 | Yoon | 5,807,393 A | 9/1998 | Williamson et al. |
| 5,637,090 A | 6/1997 | McGee et al. | 5,807,395 A | 9/1998 | Mulier et al. |
| 5,642,736 A | 7/1997 | Avitall | 5,810,802 A | 9/1998 | Panescu et al. |
| 5,643,197 A | 7/1997 | Brucker et al. | 5,810,804 A | 9/1998 | Gough et al. |
| 5,649,957 A | 7/1997 | Levin | 5,810,805 A | 9/1998 | Sutcu et al. |
| 5,655,219 A | 8/1997 | Jusa et al. | 5,810,811 A | 9/1998 | Yates et al. |
| 5,656,029 A | 8/1997 | Imran et al. | 5,814,028 A | 9/1998 | Swartz et al. |
| 5,658,278 A | 8/1997 | Imran et al. | 5,817,091 A | 10/1998 | Nardella et al. |
| 5,671,747 A | 9/1997 | Connor | 5,823,955 A | 10/1998 | Kuck et al. |
| 5,672,174 A | 9/1997 | Gough et al. | 5,823,956 A | 10/1998 | Roth et al. |
| 5,673,695 A | 10/1997 | McGee et al. | 5,827,216 A | 10/1998 | Igo et al. |
| 5,674,220 A | 10/1997 | Fox et al. | 5,829,447 A | 11/1998 | Stevens et al. |
| 5,676,662 A | 10/1997 | Fleischhacker et al. | 5,836,947 A | 11/1998 | Fleischman et al. |

| | | | | | | |
|---|---|---|---|---|---|---|
| 5,840,030 A | 11/1998 | Ferek-Petric et al. | 5,954,661 A | 9/1999 | Greenspon et al. | |
| 5,842,984 A | 12/1998 | Avitall | 5,954,665 A | 9/1999 | Ben-Haim | |
| 5,843,075 A | 12/1998 | Taylor | 5,961,514 A | 10/1999 | Long et al. | |
| 5,843,122 A | 12/1998 | Riza | 5,967,976 A | 10/1999 | Larsen | |
| 5,844,349 A | 12/1998 | Oakley et al. | 5,971,980 A | 10/1999 | Sherman | |
| 5,846,187 A | 12/1998 | Wells et al. | 5,971,983 A | 10/1999 | Lesh | |
| 5,846,191 A | 12/1998 | Wells et al. | 5,972,026 A | 10/1999 | Laufer et al. | |
| 5,846,238 A | 12/1998 | Jackson et al. | 5,980,516 A | 11/1999 | Mulier et al. | |
| 5,849,011 A | 12/1998 | Jones et al. | 5,980,517 A | 11/1999 | Gough | |
| 5,849,020 A | 12/1998 | Long et al. | 5,984,281 A | 11/1999 | Hacker et al. | |
| 5,849,028 A | 12/1998 | Chen | 5,993,447 A | 11/1999 | Blewett et al. | |
| 5,853,411 A | 12/1998 | Whayne et al. | 5,997,533 A | 12/1999 | Kuhns | |
| 5,855,590 A | 1/1999 | Malecki et al. | 6,007,499 A | 12/1999 | Martin et al. | |
| 5,855,614 A | 1/1999 | Stevens et al. | 6,010,516 A | 1/2000 | Hulka | |
| 5,860,975 A | 1/1999 | Goble et al. | 6,010,531 A | 1/2000 | Donlon et al. | |
| 5,863,290 A | 1/1999 | Gough et al. | 6,012,457 A | 1/2000 | Lesh | |
| 5,863,291 A | 1/1999 | Schaer | 6,013,074 A | 1/2000 | Taylor | |
| 5,868,737 A | 2/1999 | Taylor et al. | 6,016,809 A | 1/2000 | Mulier et al. | |
| 5,871,483 A | 2/1999 | Jackson et al. | 6,016,811 A | 1/2000 | Knopp et al. | |
| 5,871,523 A | 2/1999 | Fleischman et al. | 6,017,358 A | 1/2000 | Yoon et al. | |
| 5,871,525 A | 2/1999 | Edwards et al. | 6,023,638 A | 2/2000 | Swanson | |
| 5,873,845 A | 2/1999 | Cline et al. | 6,024,740 A | 2/2000 | Lesh et al. | |
| 5,873,896 A | 2/1999 | Ideker | 6,024,741 A | 2/2000 | Williamson et al. | |
| 5,876,398 A | 3/1999 | Mulier et al. | 6,030,403 A | 2/2000 | Long et al. | |
| 5,876,399 A | 3/1999 | Chia et al. | 6,033,402 A | 3/2000 | Tu et al. | |
| 5,876,400 A | 3/1999 | Songer | 6,036,670 A | 3/2000 | Wijeratne et al. | |
| 5,876,401 A | 3/1999 | Schulze et al. | 6,036,706 A * | 3/2000 | Morejohn et al. | 606/158 |
| 5,879,295 A | 3/1999 | Li et al. | 6,039,731 A | 3/2000 | Taylor et al. | |
| 5,879,296 A | 3/1999 | Ockuly et al. | 6,039,733 A | 3/2000 | Buyssee et al. | |
| 5,881,732 A | 3/1999 | Sung et al. | 6,039,748 A | 3/2000 | Savage et al. | |
| 5,882,346 A | 3/1999 | Pomeranz et al. | 6,042,556 A | 3/2000 | Beach et al. | |
| 5,885,278 A | 3/1999 | Fleischman | 6,047,218 A | 4/2000 | Whayne et al. | |
| 5,891,135 A | 4/1999 | Jackson et al. | 6,048,329 A | 4/2000 | Thompson et al. | |
| 5,891,136 A | 4/1999 | McGee et al. | 6,050,996 A | 4/2000 | Schmaltz et al. | |
| 5,891,138 A | 4/1999 | Tu et al. | 6,063,081 A | 5/2000 | Mulier et al. | |
| 5,893,848 A | 4/1999 | Negus et al. | 6,064,902 A | 5/2000 | Haissaguerre et al. | |
| 5,893,863 A | 4/1999 | Yoon | 6,068,653 A | 5/2000 | LaFontaine | |
| 5,895,417 A | 4/1999 | Pomeranz et al. | 6,071,279 A | 6/2000 | Whayne et al. | |
| 5,897,553 A | 4/1999 | Mulier et al. | 6,071,281 A | 6/2000 | Burnside et al. | |
| 5,897,554 A | 4/1999 | Chia et al. | 6,083,150 A | 7/2000 | Aznoian et al. | |
| 5,899,898 A | 5/1999 | Arless et al. | 6,083,222 A | 7/2000 | Klein et al. | |
| 5,899,899 A | 5/1999 | Arless et al. | 6,088,894 A | 7/2000 | Oakley | |
| 5,902,289 A | 5/1999 | Swartz et al. | 6,096,037 A | 8/2000 | Mulier et al. | |
| 5,904,711 A | 5/1999 | Flom et al. | 6,102,909 A * | 8/2000 | Chen et al. | 606/45 |
| 5,906,580 A | 5/1999 | Kline-Schoder et al. | 6,110,098 A | 8/2000 | Renirie et al. | |
| 5,906,587 A | 5/1999 | Zimmon | 6,113,592 A | 9/2000 | Taylor | |
| 5,906,606 A | 5/1999 | Chee et al. | 6,113,595 A | 9/2000 | Muntermann | |
| 5,908,029 A | 6/1999 | Knudson et al. | 6,113,598 A | 9/2000 | Baker | |
| 5,910,129 A | 6/1999 | Koblish et al. | 6,117,101 A | 9/2000 | Diederich et al. | |
| 5,913,855 A | 6/1999 | Gough et al. | 6,120,496 A | 9/2000 | Whayne et al. | |
| 5,916,213 A | 6/1999 | Haissaguerre et al. | 6,123,703 A | 9/2000 | Tu et al. | |
| 5,916,214 A | 6/1999 | Cosio et al. | 6,126,658 A | 10/2000 | Baker | |
| 5,921,924 A | 7/1999 | Avitall | 6,129,662 A | 10/2000 | Li et al. | |
| 5,921,982 A | 7/1999 | Lesh et al. | 6,142,993 A | 11/2000 | Whayne et al. | |
| 5,924,424 A | 7/1999 | Stevens et al. | 6,142,994 A | 11/2000 | Swanson et al. | |
| 5,925,038 A | 7/1999 | Panescu et al. | 6,146,394 A * | 11/2000 | Morejohn et al. | 606/158 |
| 5,925,042 A | 7/1999 | Gough et al. | 6,152,920 A | 11/2000 | Thompson et al. | |
| 5,927,284 A | 7/1999 | Borst et al. | 6,156,033 A | 12/2000 | Tu et al. | |
| 5,928,138 A | 7/1999 | Knight et al. | 6,161,543 A | 12/2000 | Cox et al. | |
| 5,928,191 A | 7/1999 | Houser et al. | 6,162,220 A | 12/2000 | Nezhat | |
| 5,928,229 A | 7/1999 | Gough et al. | 6,165,174 A | 12/2000 | Jacobs et al. | |
| 5,928,253 A * | 7/1999 | Sherman et al. ............. 606/151 | 6,185,356 B1 | 2/2001 | Parker et al. | |
| 5,931,810 A | 8/1999 | Grabek | 6,193,713 B1 | 2/2001 | Geistert et al. | |
| 5,931,836 A | 8/1999 | Hatta et al. | 6,203,557 B1 | 3/2001 | Chin | |
| 5,931,848 A | 8/1999 | Saadat | 6,206,823 B1 | 3/2001 | Kolata et al. | |
| 5,935,126 A | 8/1999 | Riza | 6,217,528 B1 | 4/2001 | Koblish et al. | |
| 5,938,660 A | 8/1999 | Swartz et al. | 6,217,576 B1 | 4/2001 | Tu et al. | |
| 5,941,251 A | 8/1999 | Panescu et al. | 6,224,592 B1 | 5/2001 | Eggers et al. | |
| 5,941,845 A | 8/1999 | Tu et al. | 6,231,518 B1 | 5/2001 | Grabek et al. | |
| 5,944,718 A | 8/1999 | Austin et al. | 6,235,024 B1 | 5/2001 | Tu | |
| 5,947,938 A | 9/1999 | Swartz et al. | 6,237,605 B1 | 5/2001 | Vaska et al. | |
| 5,951,547 A | 9/1999 | Gough et al. | 6,238,347 B1 | 5/2001 | Nix et al. | |
| 5,951,552 A | 9/1999 | Long et al. | 6,238,393 B1 | 5/2001 | Mulier et al. | |

| Patent No. | Date | Inventor |
|---|---|---|
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,264,087 B1 | 7/2001 | Whitman |
| 6,264,670 B1 | 7/2001 | Chin |
| 6,267,761 B1 | 7/2001 | Ryan |
| 6,270,471 B1 | 8/2001 | Hechel et al. |
| 6,270,497 B1 * | 8/2001 | Sekino et al. .................. 606/42 |
| 6,273,887 B1 * | 8/2001 | Yamauchi et al. ............. 606/48 |
| 6,277,117 B1 | 8/2001 | Tetzlaff et al. |
| 6,292,678 B1 | 9/2001 | Hall et al. |
| 6,293,943 B1 | 9/2001 | Panescu et al. |
| 6,296,619 B1 | 10/2001 | Brisken et al. |
| 6,296,640 B1 | 10/2001 | Wampler et al. |
| 6,302,880 B1 | 10/2001 | Schaer |
| 6,304,712 B1 | 10/2001 | Davis |
| 6,308,091 B1 | 10/2001 | Avitall |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier et al. |
| 6,332,089 B1 | 12/2001 | Acker et al. |
| 6,332,881 B1 | 12/2001 | Carner et al. |
| 6,334,860 B1 | 1/2002 | Dorn |
| 6,356,790 B1 | 3/2002 | Maguire et al. |
| 6,358,248 B1 | 3/2002 | Mulier et al. |
| 6,358,249 B1 | 3/2002 | Chen et al. |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,391,024 B1 | 5/2002 | Sun et al. |
| 6,398,792 B1 | 6/2002 | O'Connor |
| 6,409,722 B1 | 6/2002 | Hoey et al. |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,428,180 B1 | 8/2002 | Karram et al. |
| 6,430,426 B2 | 8/2002 | Avitall |
| 6,440,130 B1 | 8/2002 | Mulier et al. |
| 6,443,952 B1 | 9/2002 | Mulier et al. |
| 6,443,970 B1 | 9/2002 | Schulze et al. |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier et al. |
| 6,477,396 B1 | 11/2002 | Mest et al. |
| 6,484,727 B1 | 11/2002 | Vaska et al. |
| 6,488,678 B2 | 12/2002 | Sherman |
| 6,488,680 B1 | 12/2002 | Francischelli et al. |
| 6,502,575 B1 | 1/2003 | Jacobs et al. |
| 6,504,985 B2 | 1/2003 | Parker et al. |
| 6,506,189 B1 | 1/2003 | Rittman, III et al. |
| 6,506,200 B1 | 1/2003 | Chin |
| 6,514,250 B1 | 2/2003 | Jahns et al. |
| 6,514,252 B2 * | 2/2003 | Nezhat et al. .................. 606/48 |
| 6,517,536 B2 | 2/2003 | Hooven |
| 6,527,767 B2 | 3/2003 | Wang et al. |
| 6,537,248 B2 | 3/2003 | Mulier et al. |
| 6,537,272 B2 | 3/2003 | Christopherson et al. |
| 6,540,740 B2 | 4/2003 | Lehmann et al. |
| 6,546,935 B2 | 4/2003 | Hooven |
| 6,554,768 B1 | 4/2003 | Leonard |
| 6,558,382 B2 | 5/2003 | Jahns et al. |
| 6,575,969 B1 | 6/2003 | Rittman, III et al. |
| 6,584,360 B2 | 6/2003 | Francischelli et al. |
| 6,585,732 B2 | 7/2003 | Mulier et al. |
| 6,591,049 B2 | 7/2003 | Williams et al. |
| 6,605,084 B2 | 8/2003 | Acker et al. |
| 6,610,055 B1 | 8/2003 | Swanson et al. |
| 6,610,060 B2 | 8/2003 | Mulier et al. |
| 6,613,048 B2 | 9/2003 | Mulier et al. |
| 6,632,222 B1 | 10/2003 | Edwards et al. |
| 6,645,199 B1 | 11/2003 | Jenkins et al. |
| 6,648,883 B2 | 11/2003 | Francischelli et al. |
| 6,651,672 B2 | 11/2003 | Roth |
| 6,656,175 B2 | 12/2003 | Francischelli et al. |
| 6,663,627 B2 | 12/2003 | Francischelli et al. |
| 6,679,882 B1 | 1/2004 | Kornerup |
| 6,692,450 B1 | 2/2004 | Coleman |
| 6,692,491 B1 | 2/2004 | Phan |
| 6,699,240 B2 | 3/2004 | Francischelli et al. |
| 6,702,811 B2 | 3/2004 | Stewart et al. |
| 6,706,038 B2 | 3/2004 | Francischelli et al. |
| 6,706,039 B2 | 3/2004 | Mulier et al. |
| 6,716,211 B2 | 4/2004 | Mulier et al. |
| 6,736,810 B2 | 5/2004 | Hoey et al. |
| 6,755,827 B2 | 6/2004 | Mulier et al. |
| 6,764,487 B2 | 7/2004 | Mulier et al. |
| 6,773,433 B2 | 8/2004 | Stewart et al. |
| 6,776,780 B2 | 8/2004 | Mulier et al. |
| 6,807,968 B2 | 10/2004 | Francischelli et al. |
| 6,827,715 B2 | 12/2004 | Francischelli et al. |
| 6,849,073 B2 | 2/2005 | Hoey et al. |
| 6,858,028 B2 | 2/2005 | Mulier et al. |
| 6,887,238 B2 | 5/2005 | Jahns et al. |
| 6,899,711 B2 | 5/2005 | Stewart et al. |
| 6,911,019 B2 | 6/2005 | Mulier et al. |
| 6,916,318 B2 | 7/2005 | Francischelli et al. |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,103,947 B2 * | 9/2006 | Sartor et al. .................... 29/11 |
| 7,347,856 B2 * | 3/2008 | Wittenberger et al. ......... 606/23 |
| 2001/0031961 A1 | 10/2001 | Hooven |
| 2001/0039419 A1 | 11/2001 | Francischelli et al. |
| 2002/0002329 A1 | 1/2002 | Avitall |
| 2002/0013583 A1 * | 1/2002 | Camran et al. ................ 606/48 |
| 2002/0019629 A1 | 2/2002 | Dietz et al. |
| 2002/0032440 A1 | 3/2002 | Hooven |
| 2002/0052602 A1 | 5/2002 | Wang et al. |
| 2002/0082595 A1 | 6/2002 | Langberg et al. |
| 2002/0091382 A1 | 7/2002 | Hooven |
| 2002/0091383 A1 | 7/2002 | Hooven |
| 2002/0091384 A1 | 7/2002 | Hooven et al. |
| 2002/0099364 A1 | 7/2002 | Lalonde |
| 2002/0103484 A1 | 8/2002 | Hooven |
| 2002/0107513 A1 | 8/2002 | Hooven |
| 2002/0107514 A1 | 8/2002 | Hooven |
| 2002/0115990 A1 | 8/2002 | Acker |
| 2002/0115993 A1 | 8/2002 | Hooven |
| 2002/0120263 A1 | 8/2002 | Brown et al. |
| 2002/0120316 A1 | 8/2002 | Hooven et al. |
| 2002/0128643 A1 | 9/2002 | Simpson et al. |
| 2002/0177849 A1 | 11/2002 | Schulze et al. |
| 2002/0183738 A1 | 12/2002 | Chee et al. |
| 2003/0004507 A1 | 1/2003 | Francischelli et al. |
| 2003/0009094 A1 | 1/2003 | Segner et al. |
| 2003/0018329 A1 | 1/2003 | Hooven |
| 2003/0028187 A1 | 2/2003 | Vaska et al. |
| 2003/0032952 A1 | 2/2003 | Hooven |
| 2003/0040745 A1 | 2/2003 | Frazier et al. |
| 2003/0045871 A1 | 3/2003 | Jain et al. |
| 2003/0045872 A1 | 3/2003 | Jacobs |

| | | | |
|---|---|---|---|
| 2003/0050557 A1 | 3/2003 | Susil et al. | |
| 2003/0060822 A1 | 3/2003 | Schaer et al. | |
| 2003/0069572 A1 | 4/2003 | Wellman et al. | |
| 2003/0069577 A1 | 4/2003 | Vaska et al. | |
| 2003/0073991 A1 | 4/2003 | Francischelli et al. | |
| 2003/0078570 A1 | 4/2003 | Heiner et al. | |
| 2003/0078574 A1 | 4/2003 | Hall et al. | |
| 2003/0093104 A1 | 5/2003 | Bonner et al. | |
| 2003/0097124 A1 | 5/2003 | Lehmann et al. | |
| 2003/0100895 A1 | 5/2003 | Simpson et al. | |
| 2003/0114844 A1 | 6/2003 | Ormsby et al. | |
| 2003/0114851 A1 | 6/2003 | Truckai et al. | |
| 2003/0120268 A1 | 6/2003 | Bertolero et al. | |
| 2003/0125726 A1 | 7/2003 | Maguire et al. | |
| 2003/0125729 A1 | 7/2003 | Hooven et al. | |
| 2003/0125730 A1 | 7/2003 | Berube et al. | |
| 2003/0130598 A1 | 7/2003 | Manning et al. | |
| 2003/0135207 A1 | 7/2003 | Langberg et al. | |
| 2003/0144656 A1 | 7/2003 | Ocel | |
| 2003/0144657 A1 | 7/2003 | Bowe et al. | |
| 2003/0158548 A1 | 8/2003 | Phan et al. | |
| 2003/0171745 A1 | 9/2003 | Francischelli et al. | |
| 2003/0178032 A1 | 9/2003 | Ingle et al. | |
| 2003/0191462 A1 | 10/2003 | Jacobs | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0044340 A1 | 3/2004 | Francischelli | |
| 2004/0049179 A1 | 3/2004 | Francischelli | |
| 2004/0059324 A1 | 3/2004 | Francischelli | |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0186465 A1 | 9/2004 | Francischelli | |
| 2004/0215183 A1 | 10/2004 | Hoey | |
| 2004/0216748 A1 | 11/2004 | Chin | |
| 2004/0220560 A1 | 11/2004 | Briscoe | |
| 2004/0236322 A1 | 11/2004 | Mulier | |
| 2004/0267326 A1 | 12/2004 | Ocel | |
| 2005/0010095 A1 | 1/2005 | Stewart et al. | |
| 2005/0033280 A1 | 2/2005 | Francischelli | |
| 2005/0090815 A1 | 4/2005 | Francischelli | |
| 2005/0143729 A1 | 6/2005 | Francischelli | |
| 2005/0165392 A1 | 7/2005 | Francischelli | |
| 2005/0209564 A1 | 9/2005 | Bonner | |
| 2005/0267454 A1 | 12/2005 | Hissong | |
| 2006/0009756 A1 | 1/2006 | Francischelli | |
| 2006/0009759 A1 | 1/2006 | Christian | |

FOREIGN PATENT DOCUMENTS

| | | |
|---|---|---|
| EP | 0 450 608 | 10/1991 |
| EP | 0 765 639 | 4/1997 |
| WO | WO 92/05828 | 4/1992 |
| WO | WO 93/25267 | 12/1993 |
| WO | WO 97/10764 | 3/1997 |
| WO | WO 97/32525 | 9/1997 |
| WO | WO 98/17187 | 4/1998 |
| WO | WO 98/53750 | 12/1998 |
| WO | WO 99/02096 | 1/1999 |
| WO | WO 99/04696 | 2/1999 |
| WO | WO 99/12487 | 3/1999 |
| WO | WO 99/44519 | 9/1999 |
| WO | WO 99/56486 | 11/1999 |
| WO | WO 99/56644 | 11/1999 |
| WO | WO 99/56648 | 11/1999 |
| WO | WO 99/59486 | 11/1999 |
| WO | WO 00/21449 | 4/2000 |
| WO | WO 00/27310 | 5/2000 |
| WO | WO 00/27311 | 5/2000 |
| WO | WO 00/27312 | 5/2000 |
| WO | WO 00/27313 | 5/2000 |
| WO | WO 00/42931 | 7/2000 |
| WO | WO 00/42932 | 7/2000 |
| WO | WO 00/42933 | 7/2000 |
| WO | WO 00/42934 | 7/2000 |
| WO | WO 01/82812 | 11/2001 |
| WO | WO 01/82813 | 11/2001 |
| WO | WO 02/087454 | 11/2002 |

OTHER PUBLICATIONS

Taijiro Sueda, et al., "Efficacy of a Simple Left Atrial Procedure for Chronic Atrial Fibrillation in Mitral Valve Operations," The Annals of Thoracic Surgery, 1997, vol. 63, pp. 1070-1073.

Mien-Cheng Chen, M.D., et al., "Radiofrequency and Cryoablation of Atrial Fibrillation in Patients Undergoing Valvular Operations," Annals of Thoracic Surgery, 1998:65;1666-1672.

Arif Elvan, M.D., et al., Abstract, "Radiofrequency Catheter Ablation of the Atria Reduces Inducibility and Duration of Atrial Fibrillation in Dogs," Circulation, 1995:91:2235-2244.

Stuart P. Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiology, 2000, vol. 35 No. 2, pp. 442-450.

Akira T. Kawaguchi, et al., "Factors Affecting Rhythm After the Maze Procedure for Atrial Fibrillation", Circulation, 1996; 94(9 Suppl):II139-42.

Ivan M. Robbins, M.D., et al., "Pulmonary Vein Stenosis After Catheter Ablation of ATrial Fibrillation," Circulation, 1998; 98:1769-1775.

Enrique, J. Berjano, et al., "Bipolar Electrosurgery with Long Electrodes for RF Coagulation of Atrial Tissue," Proceedings 19$^{th}$ International Conference . . . IEEE/EMBS Oct. 30-Nov. 2, 1997 Chicago, Ill. USA, pp. 2528-2530.

Taijiro Sueda, et al., "Simple Left Atrial Procedure for Chronic Atrial Fibrillation Associated with Mitral Valve Disease," The Annals of Thoracic Surgery, 1996;62:1796-1800.

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery , vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594, (1994).

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modifications of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Suppl 1):I-493, #2889.

Cox et al., "An 8½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Curent Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

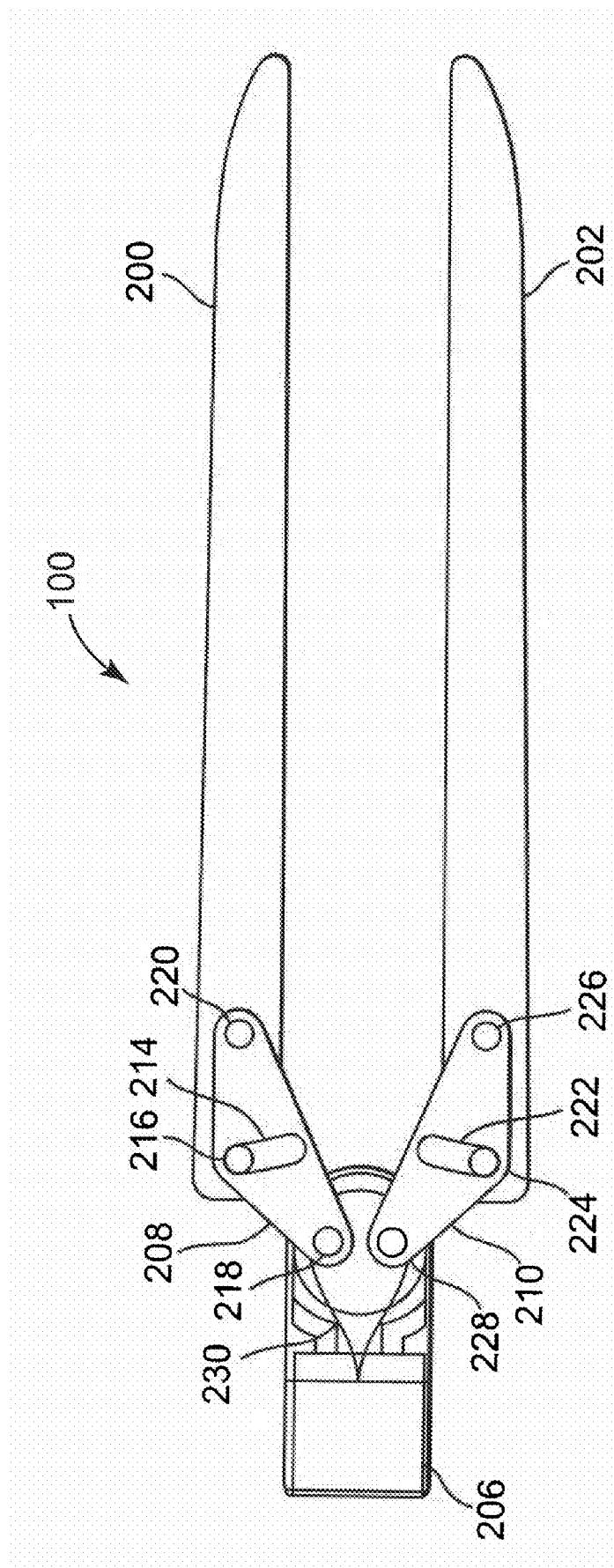

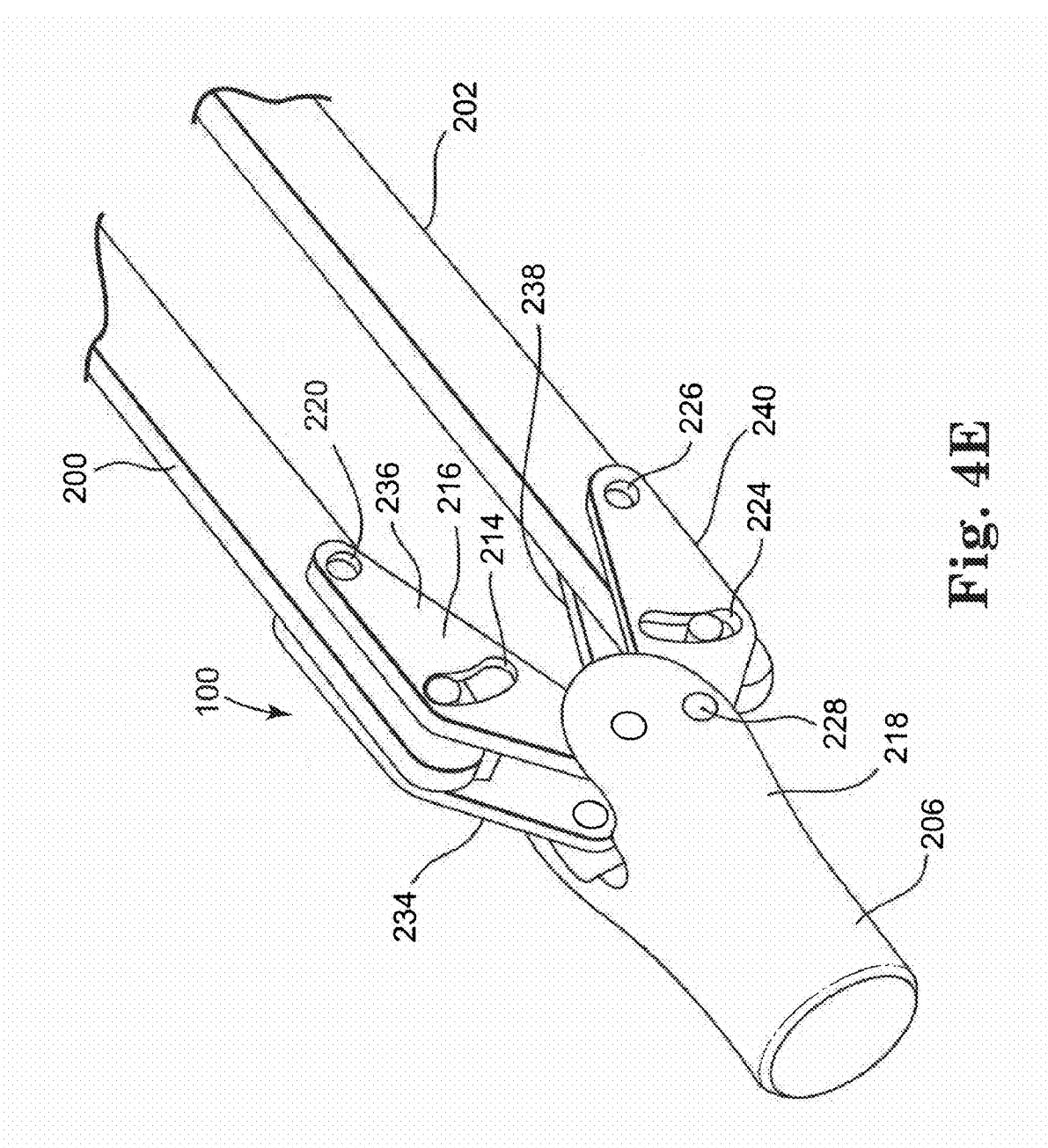

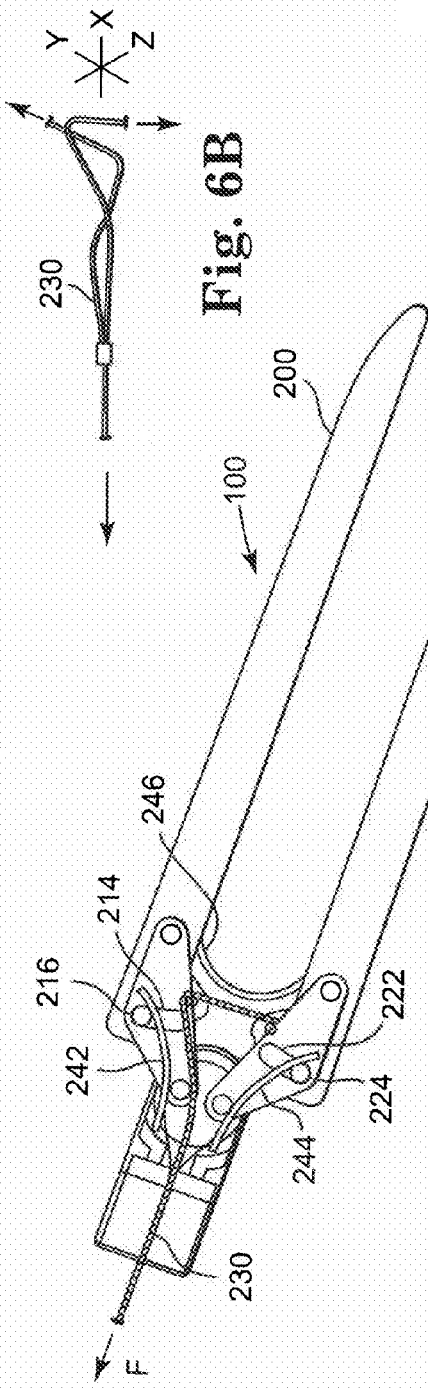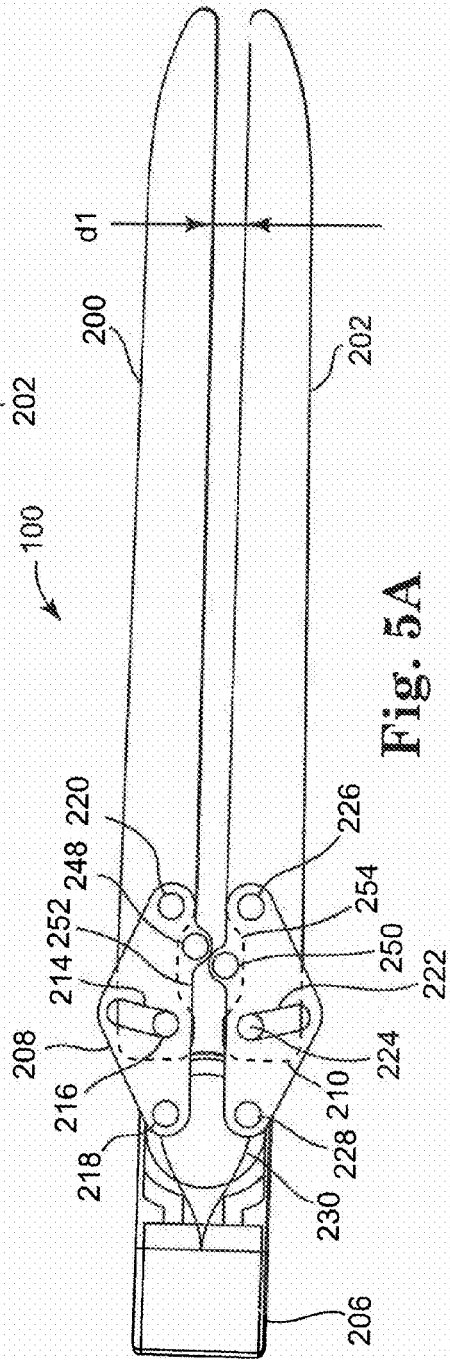
Fig. 5A
Fig. 6A
Fig. 6B

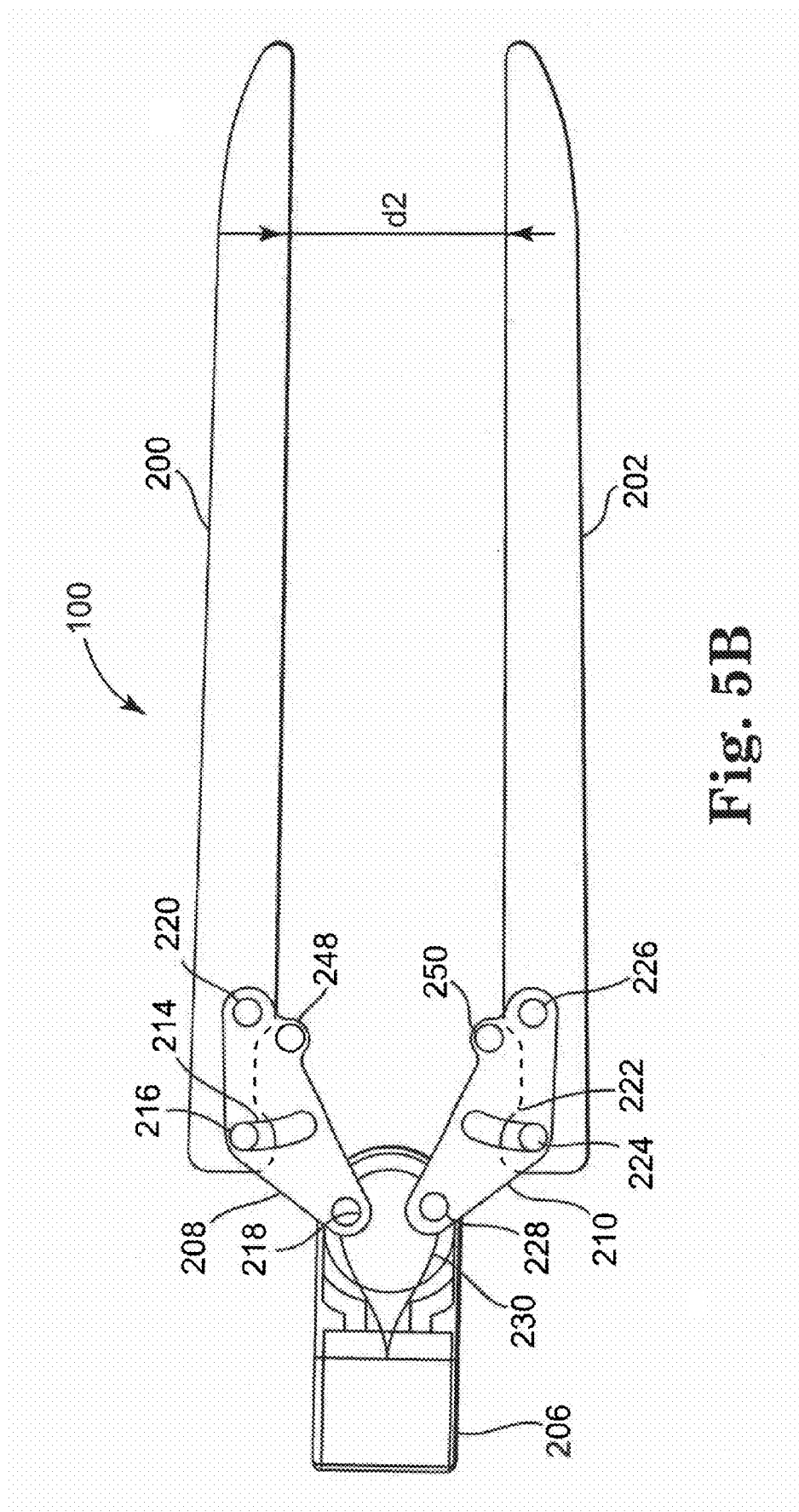

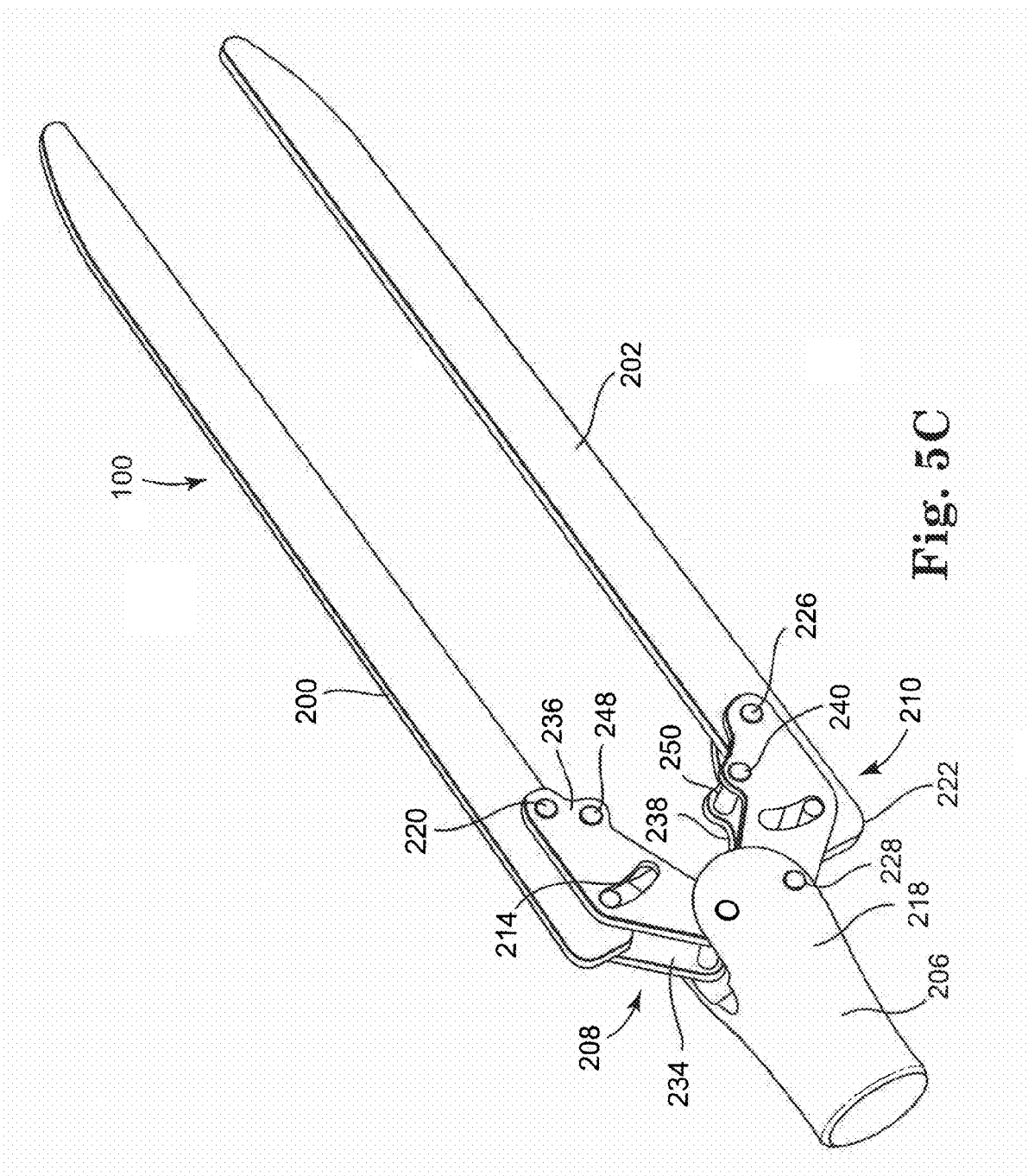

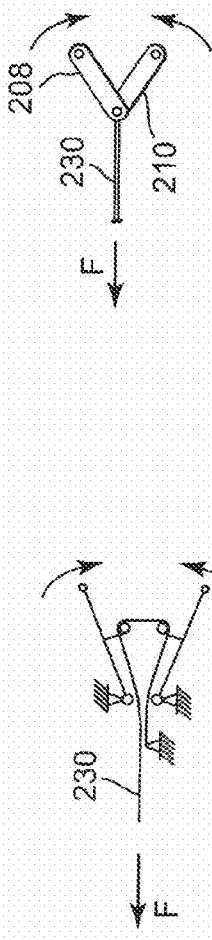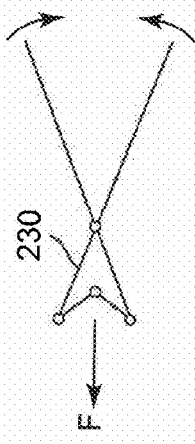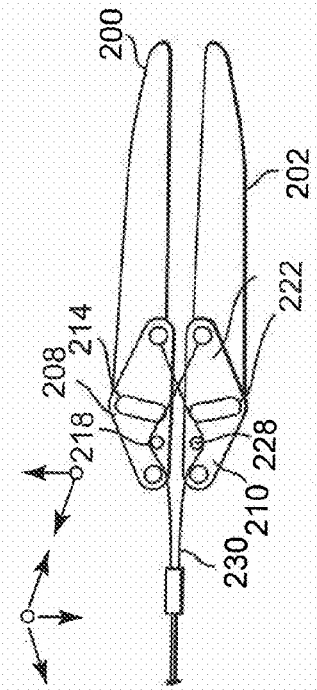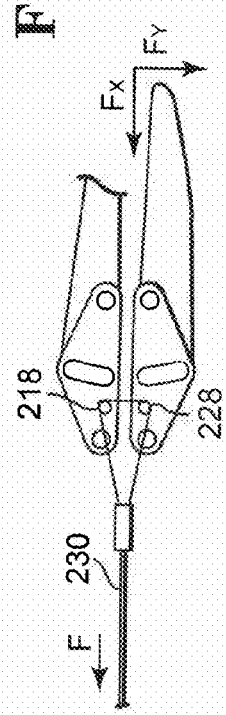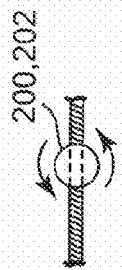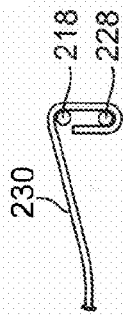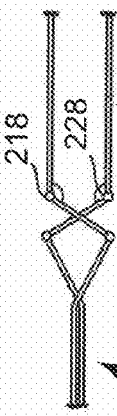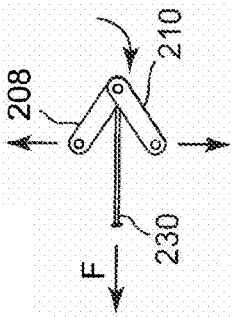

_US 7,875,028 B2_

ABLATION DEVICE WITH JAWS

RELATED APPLICATIONS

This application is a divisional of U.S. Ser. No. 11/142,954, filed on Jun. 2, 2005 now U.S. Pat. No. 7,566,334, which application claims the benefit of the filing date of U.S. Provisional Patent Application No. 60/576,096 filed on Jun. 2, 2004, which is incorporated herein by reference in its entirety; which '954 application also claims the benefit of the filing date of U.S. Provisional Patent Application No. 60/581,139 filed on Jun. 18, 2004, which is incorporated herein by reference in its entirety.

FIELD OF THE INVENTION

The invention is generally directed to ablating cardiac tissue with a minimally-invasive procedure.

BACKGROUND

The interest in ablation practice has been to use minimally-invasive techniques to ease patient recovery. Bipolar ablation devices have been used extensively to deliver linear lesions accurately to tissue especially for the purpose of reducing the effect of atrial fibrillations.

SUMMARY OF THE INVENTION

Some embodiments of the invention provide an ablation device for ablating target tissue adjacent pulmonary veins of a patient. The ablation device can include a hinge including a cam assembly, and the cam assembly can include one or more riders and one or more fingers. The ablation device can include a moving arm coupled to the hinge. The moving arm can include a cam surface that engages the riders. A floating jaw can be coupled to the moving arm. The fingers can engage the floating jaw to hold the floating jaw in a first position with respect to the moving arm. The floating jaw can include a first electrode that receives ablation energy. A lower jaw can be coupled to the hinge. The lower jaw can include a channel that receives the fingers. The channel can allow the floating jaw to move to a second position with respect to the moving arm. The lower jaw can include a second electrode that receives ablation energy.

Embodiments of the invention can provide an ablation device including a central support, an upper four-bar linkage coupled to the central support, and an upper jaw coupled to the upper linkage. The upper jaw can include an upper electrode that can receive ablation energy. The ablation device can also include a lower four-bar linkage coupled to the central support and a lower jaw coupled to the lower linkage. The lower jaw can include a lower electrode that can receive ablation energy.

One embodiment of a method of the invention can include providing an ablation device with one or more floating jaws including one or more electrodes, locking the floating jaws, and inserting the floating jaws into a side of the patient. The method can also include approaching the pulmonary veins substantially directly from the side of the patient with the floating jaws. The method can further include unlocking the floating jaws, articulating the floating jaws with respect to a central support to accommodate target tissue adjacent the pulmonary veins, and providing ablation energy to the electrodes.

One embodiment of the invention can provide an ablation system for ablating target tissue adjacent pulmonary veins of a patient through an incision in the patient. The ablation system can include an ablation tool having a handle, an upper jaw, a lower jaw, and a hinged connection. The upper jaw can include a first cannula connection, and the lower jaw can include a second cannula connection. One or more electrodes can be coupled to the upper jaw and/or the lower jaw. The electrode can receive ablation energy. The ablation system can also include a first catheter coupled to the first cannula connection. The first catheter can be inserted through the incision and can move the upper jaw adjacent the pulmonary veins. The second catheter can be coupled to the second cannula connection. The second catheter can be inserted through the incision and can move the lower jaw adjacent the pulmonary veins.

One embodiment of a method of the invention can include inserting a first catheter through an incision and positioning the first catheter on a first side of the pulmonary veins, and inserting a second catheter through the incision and positioning the second catheter on a second side of the pulmonary veins. The method can also include coupling an upper jaw of an ablation tool to the first catheter, and coupling a lower jaw of the ablation tool to the second catheter. The method can further include moving the upper jaw adjacent the pulmonary veins with the first catheter, and moving the lower jaw adjacent the pulmonary veins with the second catheter. The method can still further include providing ablation energy to one or more electrodes coupled to the upper jaw and/or the lower jaw.

BRIEF DESCRIPTION OF THE DRAWINGS

FIGS. 4A-4E are side and perspective views of an ablation device according to one embodiment of the invention.

FIGS. 5A-5D are side and perspective views of an ablation device according to one embodiment of the invention.

FIGS. 6A-6B are side and schematic views of an ablation device according to one embodiment of the invention.

FIGS. 7A-7I are side and schematic views of an ablation device according to one embodiment of the invention.

DETAILED DESCRIPTION

Figure 1:
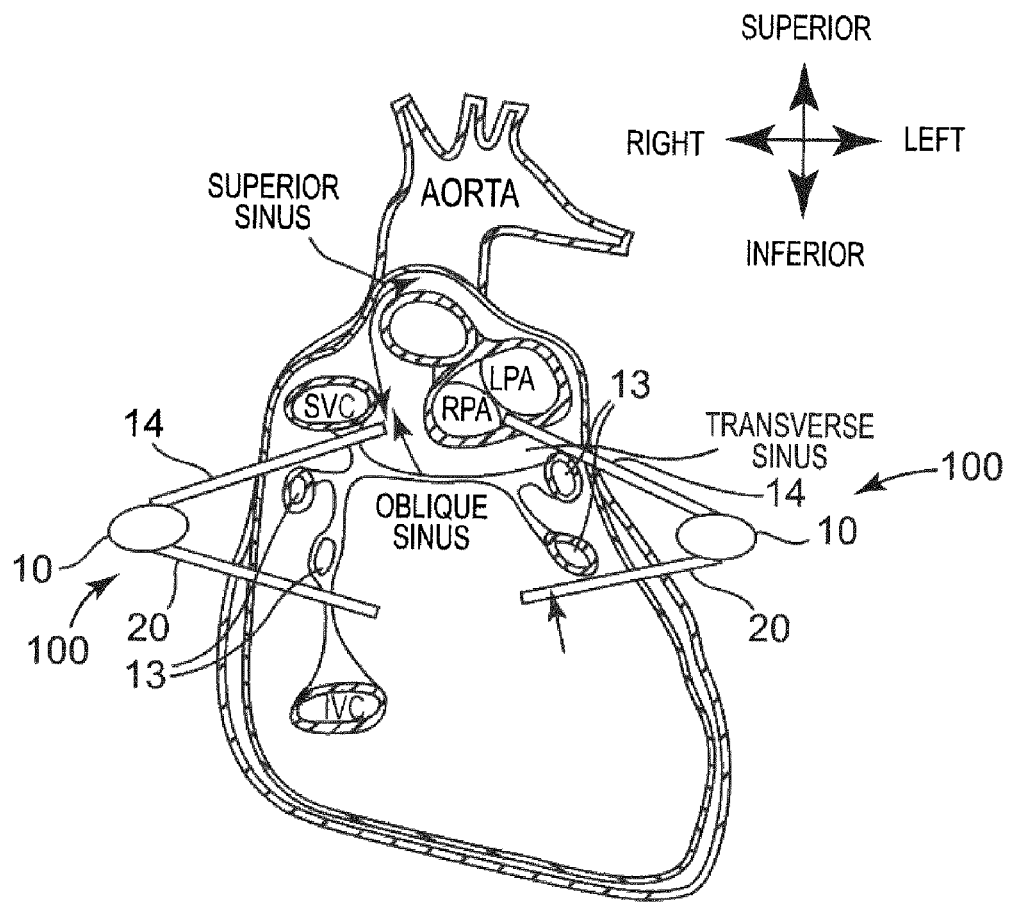
FIG. 1 is a cross-sectional view of a patient's heart and a schematic view of an ablation device according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

Some embodiments of a method of the invention provide the insertion of an ablation device having one or more electrodes on opposing jaws for clamping cardiac tissue. The electrodes can be energized with radio frequency or other energy to cause cell destruction. Some embodiments of the ablation device include jaws that can be held in place with respect to support arms, while the jaws are placed in predetermined locations along the tissue to be ablated. As the jaws are brought together, the jaws can be released from their retention position and can be allowed to float with respect to pivot points on a clamp frame in order to securely bear against and ablate the target tissue with the electrodes carried by the jaws. In one embodiment, links coupled to the jaws are spring biased to allow the jaws to move when an overriding force exerted from the clamping force overcomes the spring force.

Some embodiments of the ablation device can include a clamp-type jaw closure, including a jaw with some limited "float" to accommodate varying tissue thickness. When the jaws are fully opened, the floating jaw can be locked to prevent relative movement that could impede insertion of the ablation device into the patient's cavity. As the jaws are closed, the floating jaw can be allowed more and more relative movement to accommodate the target tissue. In some embodiments, the jaws can articulate left and right with inputs from a handle to allow additional adjustment relative to the target tissue. These additional adjustments can require bilateral access. However, the bilateral access can be achieved through ports, eliminating the need for a thoracotomy.

In one embodiment, the ablation device can include a hinge having a cam surface and one or more riders. In some embodiments, the riders can be coupled to a fixed jaw and the cam surface can be coupled to a floating jaw. In one embodiment, the cam surface can be coupled to a moving arm coupled to the floating jaw. When the jaws are separated by an angle larger than a predefined acute angle, the floating jaw can be maintained in an unyielding angular relation to the fixed jaw. As the angle between the jaws approaches the predefined acute angle, the riders and the cam surface can separate to allow the floating jaw to move with respect to the fixed jaw. The floating jaw can then bear against the target tissue at the most advantageous angle to provide maximum contact between the electrodes on the jaws and the target tissue.

Some embodiments of the ablation device can be used to approach the left pulmonary veins from a port on the left side of the patient and the right pulmonary veins from a port on the right side of the patient. Rather than approaching the pulmonary veins from an inferior or superior point as in an open chest procedure, some embodiments of the ablation device can be used to approach the pulmonary veins directly from the side.

In some embodiments, the ablation device can include two jaws that can be inserted into the patient separately and then assembled in place. This provides a simple process for insertion of the ablation device, because the surgeon can concentrate on one jaw at a time. The first jaw can be inserted from a right thoracotomy through a previously-dissected pericardial reflection under the superior vena cava into the transverse sinus until the first jaw is hooked around the left pulmonary veins into the oblique sinus. The second jaw can be inserted through the right thoracotomy below the inferior vena cava through the previously-dissected pericardial reflection and then attached to the first jaw to form a complete ablation device. Ablation can be performed in two steps. Using independent jaw closure mechanisms, the first jaw can be closed and actuated. Once the first jaw is open, the second jaw can be closed and actuated. In this manner, only half of the pulmonary veins are occluded at any given time.

Some embodiments of the invention can be used to clamp cardiac tissue and carry electrodes used to deliver radio frequency energy during an ablation procedure. Embodiments of the ablation device can include a linkage that can provide a spring-biased movement of clamping members. Clamping can start at a distal end and move progressively toward a proximal end of the clamping members. Some embodiments of the invention can provide a minimal envelope size relative to the clamping capacity. Some embodiments of the invention can be used for effectors of an ablation device. Embodiments of the invention can also be used for other applications requiring tissue clamping or manipulation. Embodiments of the ablation device can include a distal end for use in minimally-invasive cardiac surgery or in conventional cardiac surgery. For the minimally-invasive cardiac surgeries, the ablation device can include dual floating jaws. For conventional cardiac surgeries, the ablation device can include a single floating jaw and one fixed jaw. Some embodiments of the invention can include an ablation device that is spring biased or elastically biased for parallel jaw action. Embodiments of the ablation device can have a minimal size relative to the clamping capacity. Some embodiments of the ablation device provide distal to proximal progressive clamping action. Some embodiments of the ablation device can include an increased gap at a vertex of a proximal end of a jaw assembly.

FIG. 1 is a schematic illustration of two ablation devices 100 positioned within a patient's heart around pulmonary veins 13. Each one of the ablation devices 100 can include a hinge 10, a lower jaw 14, and a floating jaw 20. One ablation device 100 can be inserted into the patient's heart from a port on the patient's left side, and another ablation device 100 can be inserted into the patient's heart from a port on the patient's right side. In some embodiments, one or more ablation devices 100 can be used to access the pulmonary veins 13 from the sides of the patient through ports, which can eliminate the need for a thoracotomy. In other embodiments, one or more ablation devices 100 can be used in combination with a thoracotomy.

As shown in FIGS. 2A-2F, a drawbridge concept can incorporate a bilateral bipolar clamp into an ablation device 100 that can be used for a single-sided approach. The ablation device 100 can be used through a port on only the right side of the patient. However, the ablation device 100 can also be used through a right thoracotomy.

FIGS. 2A-2F illustrate an ablation device 100 including a hinge 10, a cam assembly 12, a lower jaw 14, one or more riders 16, a cam surface 18, a floating jaw 20, a moving arm 24, one or more fingers 26, a channel 28, and a swivel attachment 30. The moving arm 24 can be coupled to the floating jaw 20 by the swivel attachment 30. The hinge 10 can include the cam assembly 12 that can be coupled to the lower jaw 14. The cam assembly 12 can include the riders 16 and the fingers 26. The lower jaw 14 can be fixed with respect to the hinge 10 and can include the channel 28. The moving arm 24 can include the cam surface 18. The riders 16 can engage the cam surface 18 on the moving arm 24. The fingers 26 can bear against the floating jaw 20 to hold the floating jaw 20 in relation to the moving arm 24 and the lower jaw 14. As an angle between the floating jaw 20 and the lower jaw 14 reaches a predefined acute angle, the fingers 26 on the cam assembly 12 can recess into the channel 28 of the lower jaw 14 and can disengage from the floating jaw 20, allowing the floating jaw 20 to pivot about the swivel attachment 30.

Figure 2A:
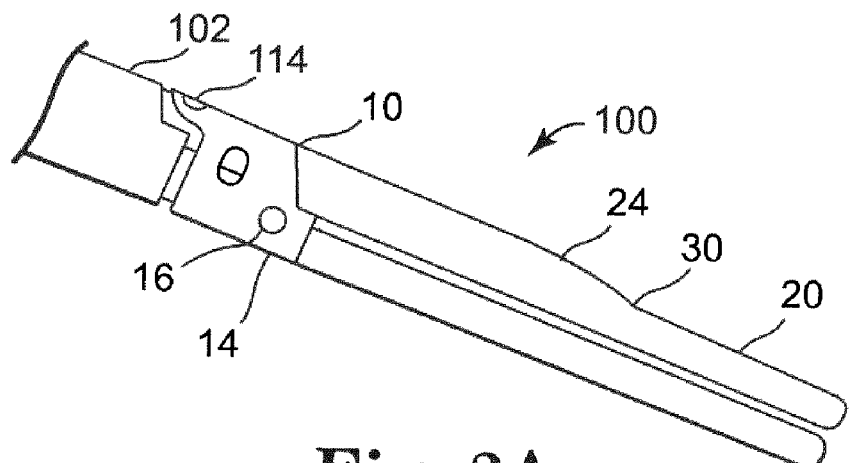
FIGS. 2A-2F are perspective views of an ablation device according to one embodiment of the invention.
Figure 2B:
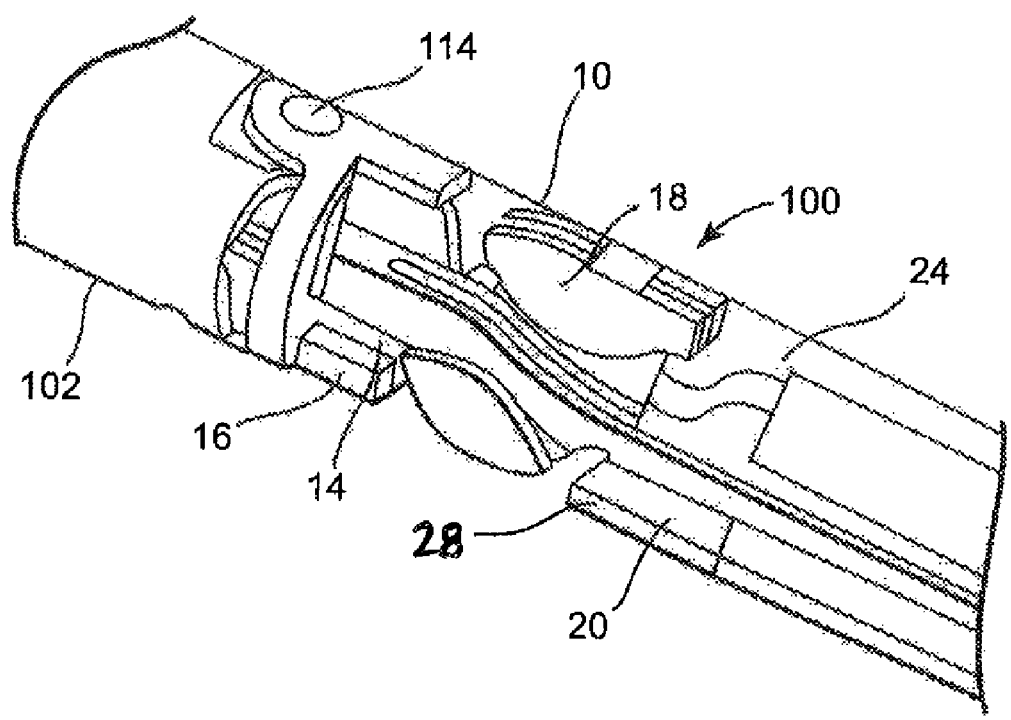
Figure 2C:
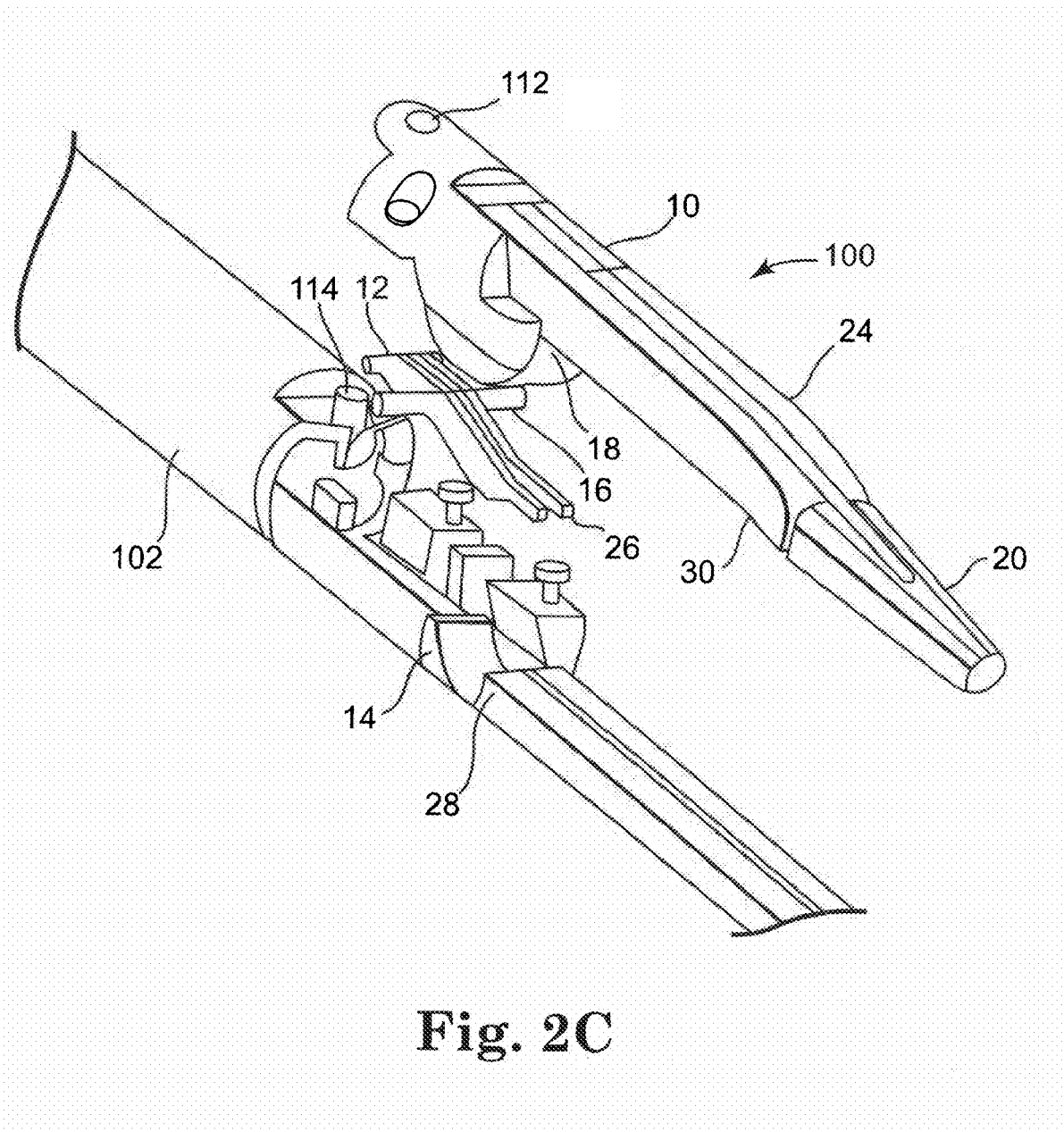

FIG. 2A illustrates the ablation device 100 with the lower jaw 14 substantially in contact with the floating jaw 20. In the position shown in FIG. 2A, the ablation device 100 can be inserted into the patient's body through a port or a thoracotomy. FIG. 2B illustrates the hinge 10 in a substantially closed position. FIG. 2C is an exploded view of the hinge 10 in the substantially closed position. The fingers 26 of the cam assembly 12 can bear against the floating jaw 20 to hold it in relation to the moving arm 24. As the predefined acute angle between the floating jaw 20 and the lower jaw 14 is reached, the fingers 26 of the cam assembly 12 can engage the channel 28 on the lower jaw 14. The fingers 26 can then disengage from the floating jaw 20 in order to allow the floating jaw 20 to pivot about the swivel attachment 30.

Figure 2D:
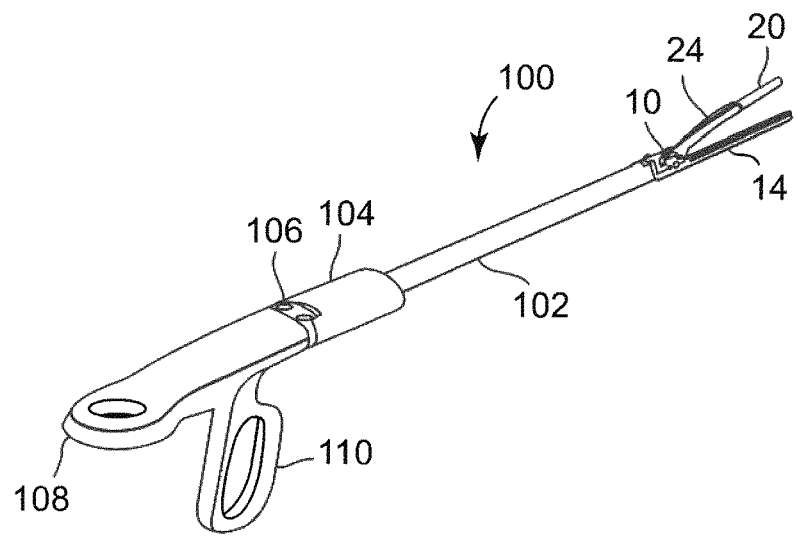
Figure 2E:
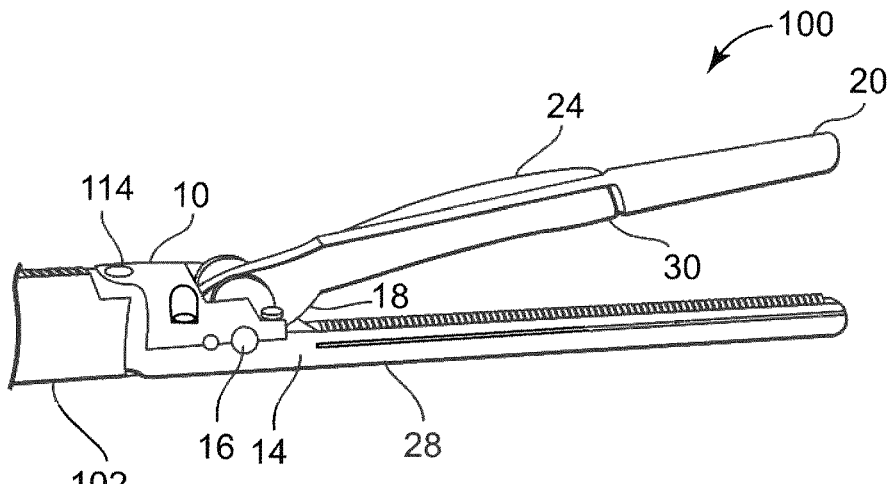
Figure 2F:
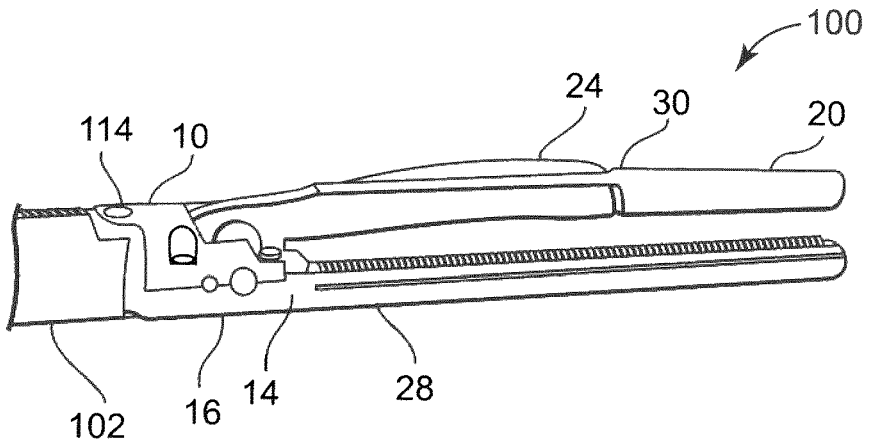

As shown in FIG. 2C, the hinge 10 can include an aperture 112 that can receive a protrusion 114 of a neck 102. FIG. 2D illustrates the ablation device 100 including the neck 102, a collar 104, a hinge assembly 106, a thumb ring 108, and a trigger 110. In some embodiments, the ablation device 100 can be rotated about the hinge assembly 106. In some embodiments, the surgeon can place his or her thumb through the thumb ring 108 and his or her fingers through the trigger 110. The trigger 110 can be coupled via a wire or a cable (not shown) to the floating jaw 20 and the moving arm 24 in order to control the movement of the floating arm 20 and/or the moving arm 24. FIG. 2E illustrates the ablation device 100 in a substantially open position. FIG. 2F illustrates the ablation device 100 in a partially-open position.

Figure 3A:
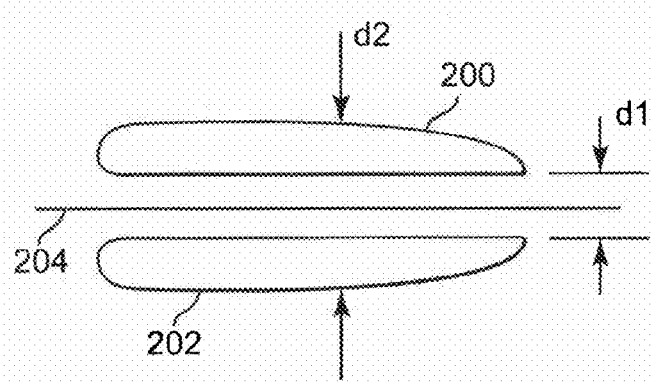
FIGS. 3A-3E are side and schematic views of an ablation device according to one embodiment of the invention.
Figure 3B:
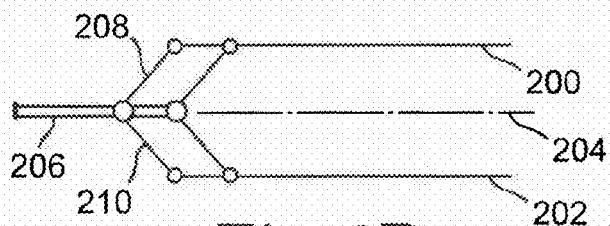

FIGS. 3A-3E illustrate an embodiment of an ablation device 100 including an upper jaw 200 and a lower jaw 202. As shown in FIGS. 3A and 3B, the upper jaw 200 can be positioned in a parallel relationship to the law jaw 202 about an axis 204. The upper jaw 200 can be positioned a distance $d_1$ from the lower jaw 202, with the distance $d_1$ being within a range of approximately 12 mm to approximately 15 mm. The outer portions of the upper jaw 200 and the lower jaw 202 can be separated by a distance $d_2$. FIG. 3B illustrates an embodiment of the ablation device 100 including the upper jaw 200 and the lower jaw 202 coupled to a central support 206. The upper jaw 200 can be coupled to the central support 206 with an upper four-bar linkage 208. The lower jaw 202 can be coupled to the central support 206 with a lower four-bar linkage 210.

Figure 3C:
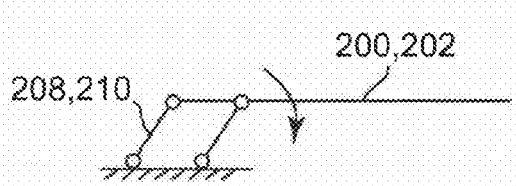
Figure 3D:
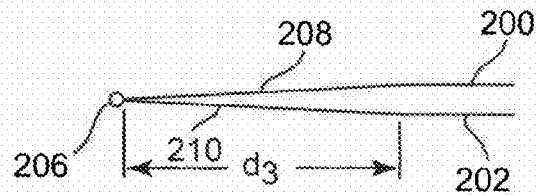
Figure 3E:
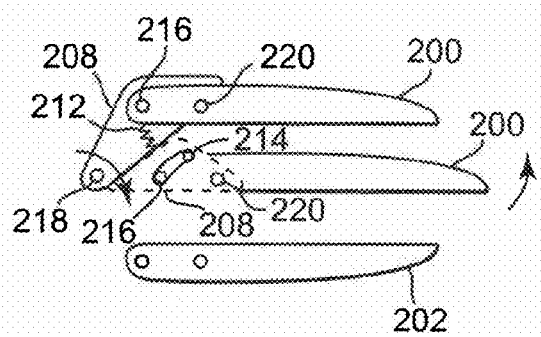

FIG. 3C illustrates forces on a four-bar linkage 208 or 210, with the grounded portion indicating the position of the central support 206. FIG. 3D illustrates a distance $d_3$ between the central support 206 and the upper jaw 200 and the lower jaw 202. The distance $d_3$ can represent a distance occupied by the upper four-bar linkage 208 and/or the lower four-bar linkage 210. FIG. 3E illustrates the upper jaw 200 coupled to an upper four-bar linkage 208 that can be biased with a spring 212 and can include an aperture 214. The aperture 214 can receive a first pin 216. The four-bar linkage 208 can pivot about a pivot point 218. A second pin 220 can be coupled between the upper jaw 200 and the upper four-bar linkage 208. The spring 212 can include a coil spring, a torsional spring, a beam spring, or any other suitable biasing member. The spring 212 can bias the upper jaw 200 to a near parallel position with the lower jaw 202 when the jaws are in their open position. Due to the configuration of the aperture 214, the upper jaw 200 can begin a clamping action at its distal end and can finish the clamping action at its proximal end. The upper four-bar linkage 208 can be designed in order to limit rotation in a downward direction. In some embodiments, the upper jaw 200 can be a moveable jaw, while the lower jaw 202 can be fixed. In other embodiments, both the upper jaw 200 and the lower jaw 202 can move.

FIGS. 4A-4E illustrate another embodiment of the ablation device 100 including a movable upper jaw 200 and a movable lower jaw 202. In one embodiment, the upper jaw 200 and/or the lower jaw 202 can be constructed of a substantially malleable material. The upper jaw 200 can be connected to a central support 206 by an upper four-bar linkage 208. The upper four-bar linkage 208 can include a first aperture 214, which can receive a first pin 216. The upper four-bar linkage 208 can also be coupled to the upper jaw 200 with a second pin 220. The upper four-bar linkage 208 can be coupled to the central support 206 and can pivot about a first pivot 218. The lower jaw 202 can be coupled to the central support 206 with a lower four-bar linkage 210. The lower four-bar linkage can include a second aperture 222 that can receive a third pin 224. The lower four-bar linkage 210 can also be coupled to the lower jaw 202 with a fourth pin 226. The lower four-bar linkage 210 can pivot with respect to the central support 206 via a second pivot 228. The ablation device 100 can also include a cable or wire 230 which can be positioned around the first pivot 218 and the second pivot 228 and can continue through the central support 206. Proximal ends of the wire or cable 230 can be connected to an actuator device (not shown).

Figure 4B:
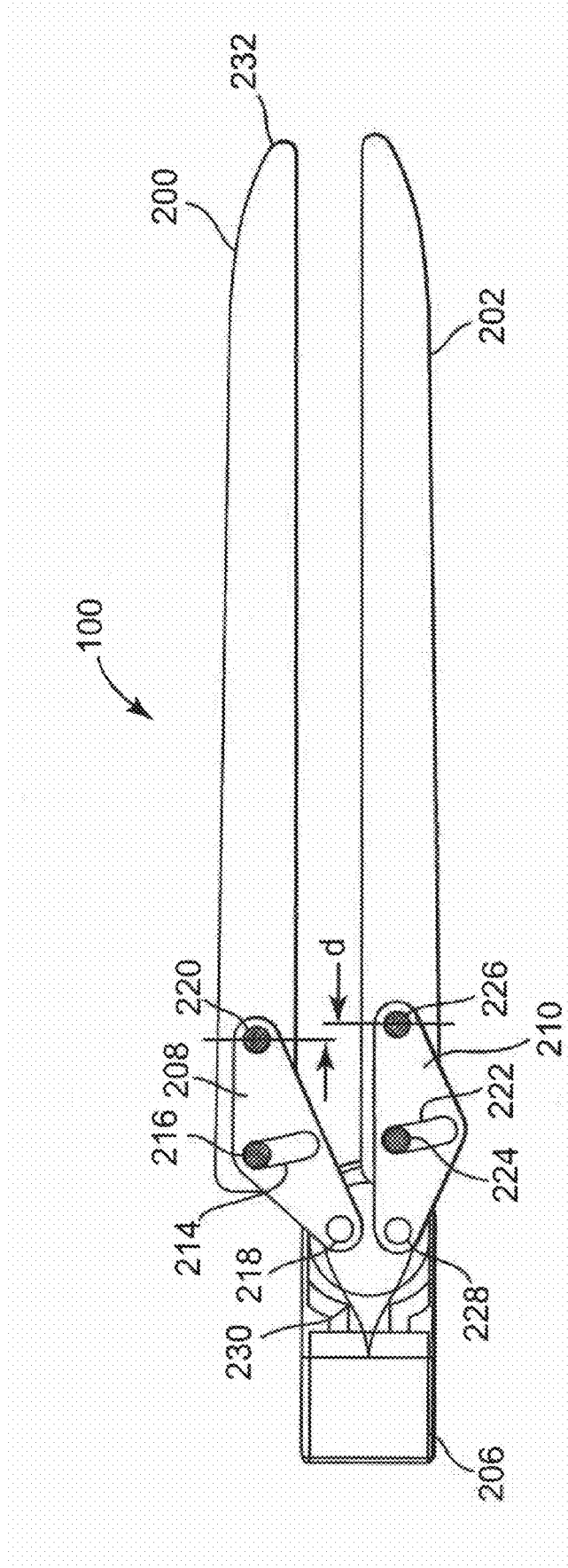

FIG. 4B illustrates the upper jaw 200 in its open position and the lower jaw 202 in its closed position. First pin 216 can be located in an upper portion of the first aperture 214 when the upper jaw 200 is in its open position. The first pin 216 can be biased into the upper portion of the first aperture 214 by a spring or other biasing member, which can make a distal end 232 of the upper jaw 200 come into contact with the target tissue first. The third pin 224 is shown in FIG. 4B in an upper position within the second aperture 222 when the lower jaw 202 is in its closed position. In this manner, the upper jaw 200 and the lower jaw 202 can be constrained by the movement of the first pin 216 within the first aperture 214 and the third pin 224 within the second aperture 222. The first aperture 214 and the second aperture 222 can be designed to provide any desirable gap between the upper jaw 200 and the lower jaw 202. The first aperture 214 and the second aperture 222 can be designed in order to provide a distance d between the second pin 220 and the fourth pin 226 when the upper jaw 200 is in its open position and the lower jaw 202 is in its closed position. This distance d can represent a forward travel of the upper and lower jaws in their closed positions. The cable or wire 230 can provide a means to index the upper jaw 200 and lower jaw 202 relative to a handle (not shown) coupled to the central support 206.

Figure 4C:
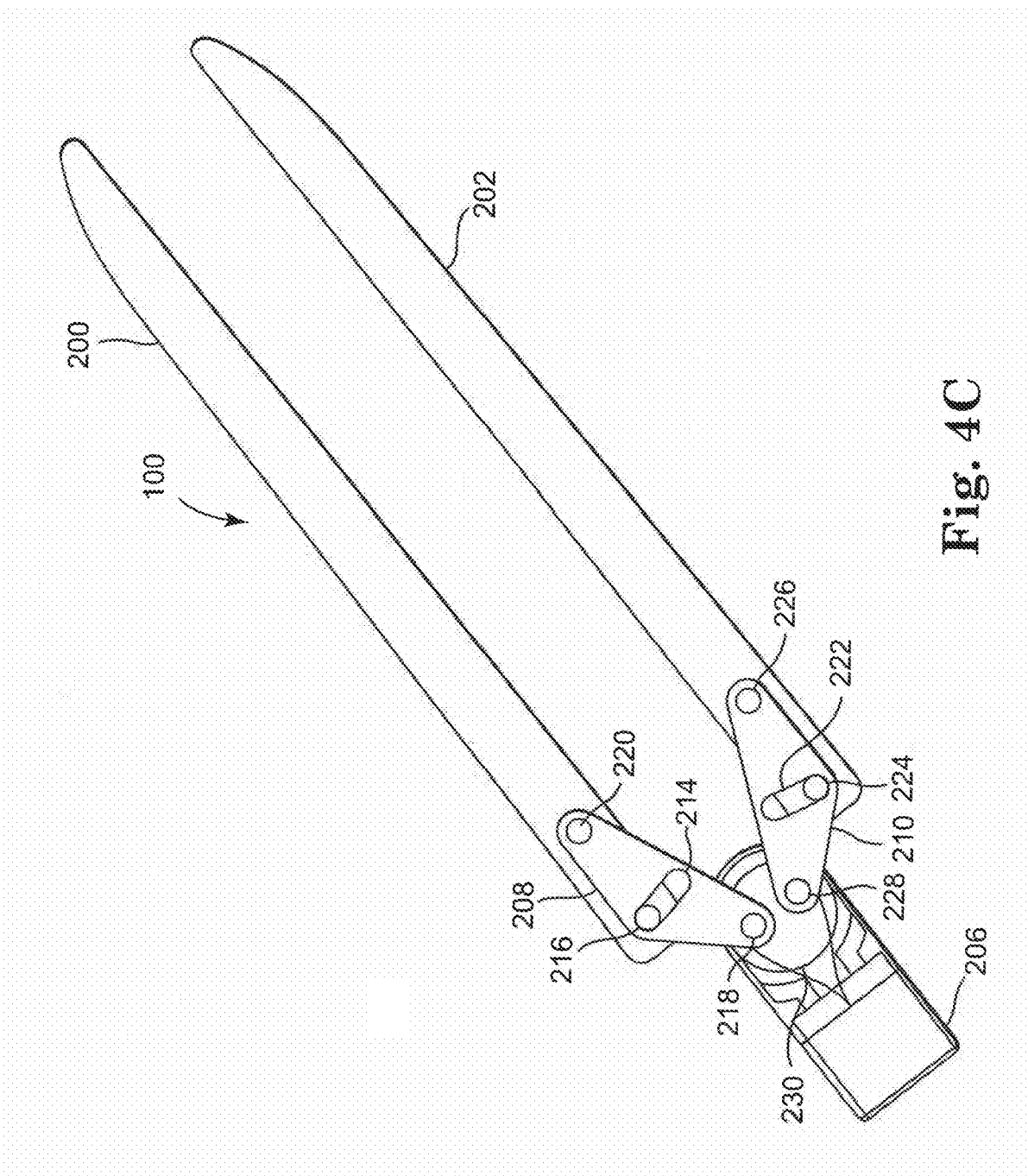
Figure 4D:
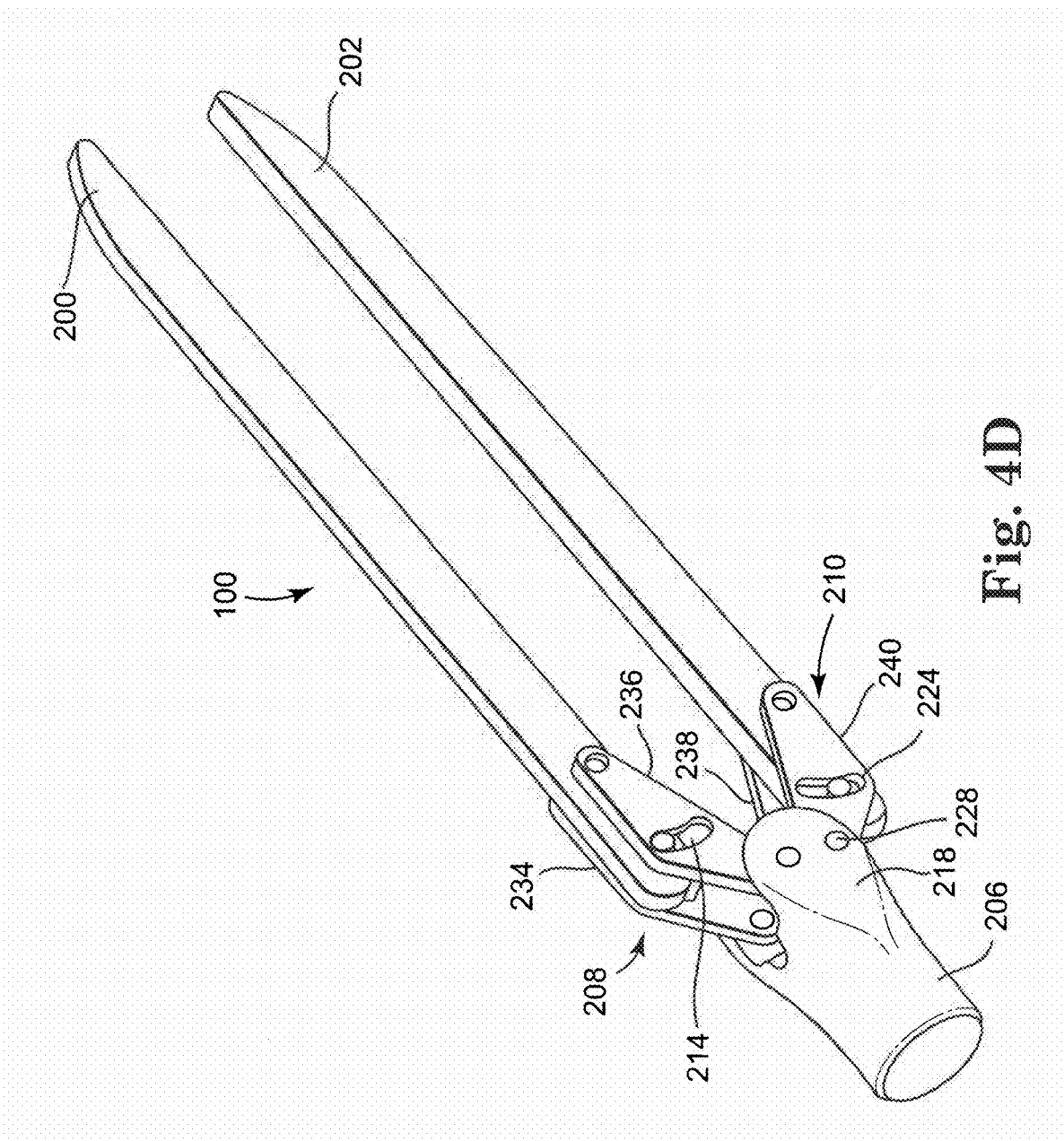

FIG. 4C is a line diagram of the ablation apparatus 100, while FIG. 4D is a solid model diagram of the ablation device 100. FIG. 4D illustrates that the upper four-bar linkage 208 and the lower four-bar linkage 210 can each include two links. For example, the upper four-bar linkage 208 can include a first link 234 and a second link 236, and the lower four-bar linkage 210 can include a third link 238 and a fourth link 240. The four-bar linkages 208 and 210 with multiple links can also include the appropriate number of apertures and pins in order to couple the four-bar linkages to the central support 206 and the upper jaw 200 and the lower jaw 202. However, some embodiments of the ablation device 100 can include only a single link for the upper four-bar linkage 208 and/or only a single link for the lower four-bar linkage 210. FIG. 4E is another solid model diagram of the ablation device 100. FIG. 4E also illustrates the upper four-bar linkage 208 including two links and the lower four-bar linkage 210 including two links.

FIGS. 5A through 5D illustrate an embodiment of the ablation device 100 including an upper four-bar linkage 208 and a lower four-bar linkage 210 with stop members 248 and 250 positioned within recesses 252 and 254. The upper stop member 248 can be included within the upper four-bar linkage 208, and the upper recess 252 can be included in the upper jaw 200. The lower stop member 250 can be included in the lower four-bar linkage 210, and the lower recess 254 can be included in the lower jaw 202. The configurations of the upper four-bar linkage 208 and the lower four-bar linkage 210 along with the upper and lower stop members 248 and 250 can allow the ablation device 100 to be in a closed position having a smaller distance $d_1$ between the upper jaw 200 and the lower jaw 202. The smaller distance $d_1$ between the upper jaw 200 and the lower jaw 202 can allow the ablation device 100 to be inserted into a smaller port in the patient's side.

Figure 5D:
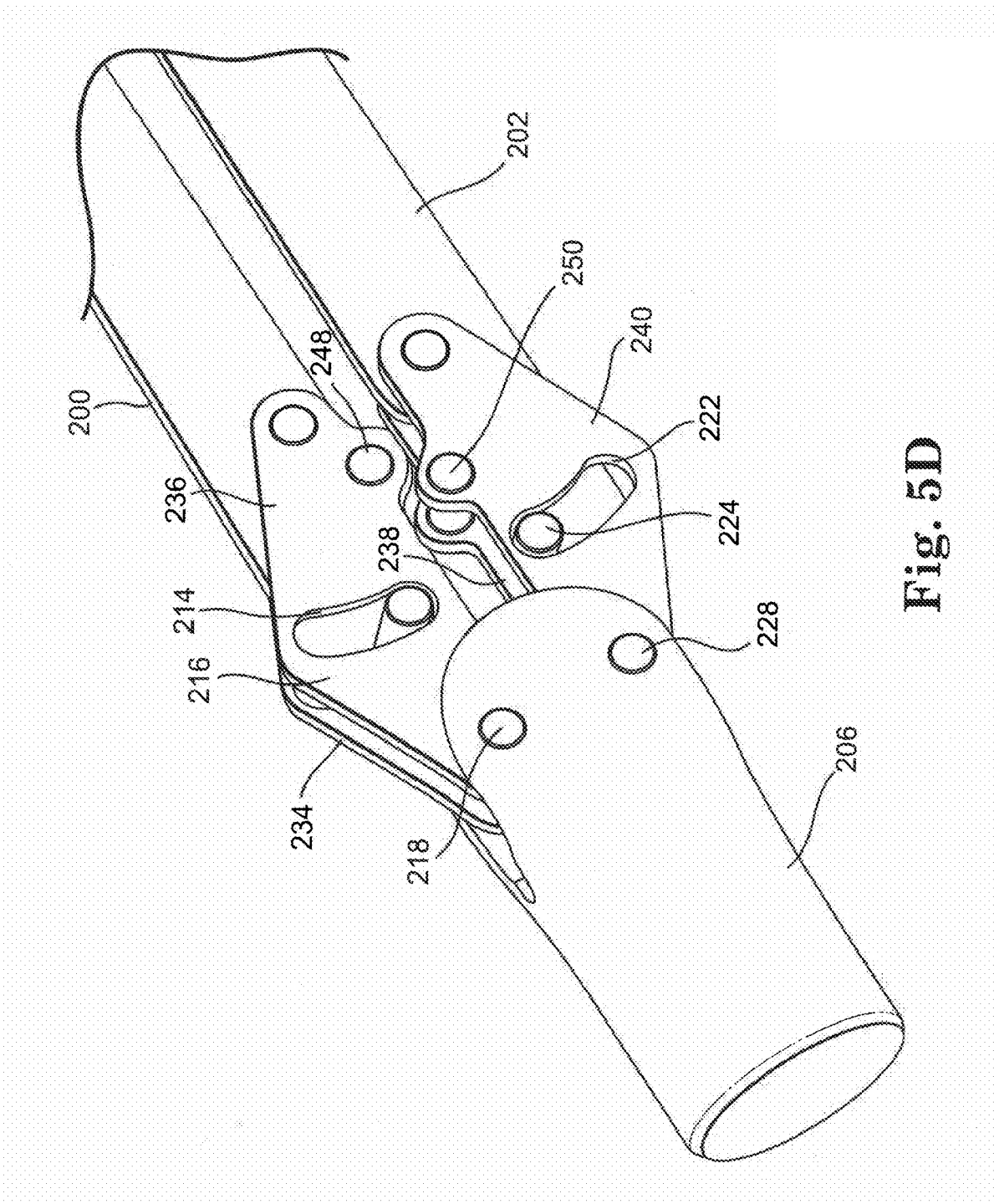

FIG. 5B illustrates the upper jaw 200 and the lower jaw 202 in their open positions with a distance $d_2$ between the upper jaw 200 and the lower jaw 202. The distance $d_1$ shown in FIG. 5A can be approximately 2 mm, in some embodiments. The distance $d_2$ shown in FIG. 5B can be approximately 15 mm, in some embodiments. FIGS. 5C and 5D are solid model diagrams of the ablation apparatus 100. FIGS. 5C and 5D illustrate that the upper four-bar linkage 208 and the lower four-bar linkage 210 can each be constructed of two links. For example, the upper four-bar linkage 208 can include a first link 234 and a second link 236, and the lower four-bar linkage 210 can include a third link 238 and a fourth link 240. As shown in FIG. 5C, the stop members 248 and 250 can be pins that can join the two links of the four-bar linkages. For example, the stop member 250 can join the third link 238 to the fourth link 240 of the lower four-bar linkage 210.

FIGS. 6A and 6B illustrate an embodiment of the wire or cable 230 wrapped around portions of the upper four-bar linkage 208 and the lower four-bar linkage 210. FIG. 6A also illustrates the use of a first spring 242 and a second spring 244 in order to bias the upper jaw 200 and the lower jaw 202. In some embodiments, the first spring 242 and the second spring 244 can bias the upper jaw 200 and the lower jaw 202 into their open positions so that the first pin 216 is in an uppermost position within the first aperture 214 and the third pin 224 is in a lowermost portion within the second aperture 222. FIG. 6A also illustrates a flexible spacer 246 that can be positioned between the upper jaw 200 and the lower jaw 202 in order to prevent tissue from being caught within the moving parts of the upper four-bar linkage 208 and the lower four-bar linkage 210. In some embodiments, the cable 230 can be split near a clevis in order to run the cable 230 on both sides of the upper jaw 200 and the lower jaw 202, for example, in order to run the cable 230 from top to bottom or from bottom to top. In some embodiments, the upper jaw 200 and the lower jaw 202 can be placed at an offset position (e.g., side-by-side) in order to reduce an overall height when introducing the ablation device 100 into the patient's body.

FIGS. 7A-7I illustrate alternative embodiments of the ablation device 100. FIG. 7A illustrates an ablation device 100 including an upper jaw 200, a lower jaw 202, an upper four-bar linkage 208, a lower four-bar linkage 210, and a cable 230 coupled between the upper and lower four-bar linkages 208, 210. The cable 230 can be wrapped around a first pivot 218 and then connected to the lower four-bar linkage 210, and then the same cable 230 can be wrapped around a second pivot 228 and connected to the upper four-bar linkage 218. In this manner, the cable 230 can form a cross-over cable system. Decreasing an angle of the cross-over cable system can increase the closing force between the upper jaw 200 and the lower jaw 202. FIG. 7B illustrates one embodiment of the cable 230 in a cross-over cable configuration.

FIG. 7C illustrates one embodiment of the cable 230 in a triangular configuration. A force exerted on the cable 230 can generate a force in along the X axis $F_x$ and a force along the Y axis $F_y$. FIG. 7D illustrates another configuration for the cable 230. The cable 230 can wrap around any suitable pivots or pins, such as the first pivot 218 and the second pivot 228. FIG. 7E illustrates another embodiment of a cross-over cable system. FIG. 7F illustrates the forces and the positions at which the cable 230 can be grounded in one embodiment of a cable system. FIGS. 7G and 7H schematically illustrate the cable 230 connected to a link of the upper four-bar linkage 208 and a link of the lower four-bar linkage 210. A higher force can be exerted by the links as shown in FIG. 7G, and a lower force can be exerted by the links as shown in FIG. 7H. FIG. 7I illustrates that, in some embodiments, the upper jaw 200 and/or the lower jaw 202 can be allowed to rotate plus or minus 30 degrees without binding the cable 230 or the cross-over cable system. In other embodiments, the cable 230 and/or a cable system can include other members, such as a toggle, a cam, or a pulley system.

FIGS. 8A-8E illustrate an embodiment of the ablation apparatus 100 including a gear 256, a stop member 258, and a socket 260. The gear 256 can include teeth that can cooperate with corresponding recesses on the socket 260 in order to perform an indexing feature for the upper jaw 200 and the lower jaw 202. The stop member 258 can prevent the gear 256 from traveling beyond a predetermined position. The upper jaw 200 and/or the lower jaw 202 can be spring loaded into an open position. Distal ends 232 of the upper jaw 200 and the lower jaw 202 can contact one another first once the spring bias has been overcome. The upper jaw 200 and the lower jaw 202 can clamp into contact progressively from the distal end 232 to their proximal ends 262.

Figure 8E:
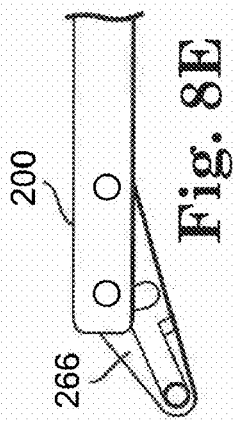
FIGS. 8A-8E are side and schematic views of an ablation device according to one embodiment of the invention.
Figure 8B:
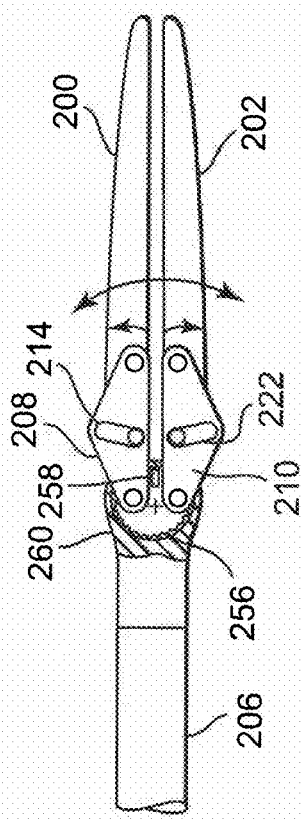
Figure 8D:
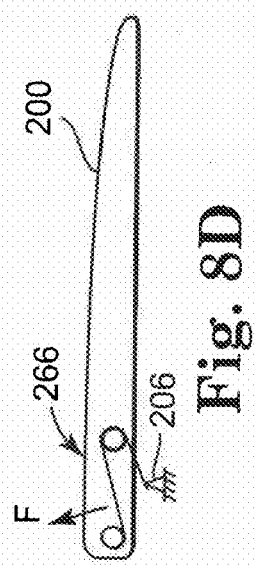
Figure 8C:
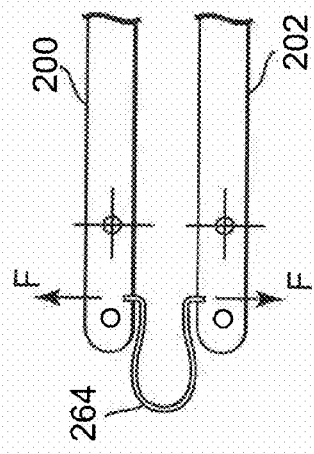
Figure 8A:
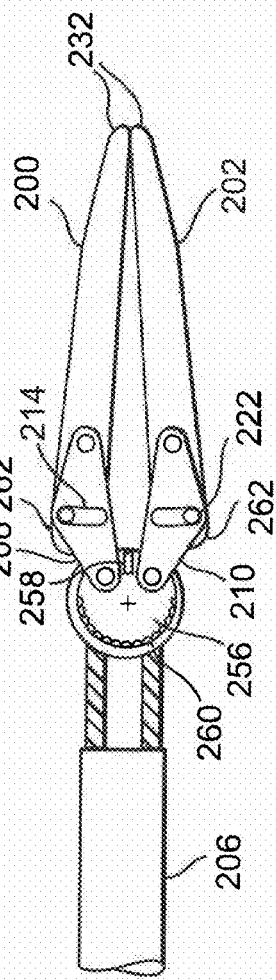

FIG. 8B illustrates that the gear 256 and the socket 260 can have a ratchet and detent configuration in order to set an angle between the upper jaw 200 and the lower jaw 202 relative to the central port 206. The angle can be plus or minus 30 degrees, in some embodiments. FIG. 8C illustrates one embodiment of a U-shaped spring 264 that can be coupled between the upper jaw 200 and the lower jaw 202. FIG. 8D illustrates an embodiment of a torsional spring 266 that can be coupled to a ground, which can represent the central support 206 and one or more pivot points on the upper jaw 200. FIG. 8E illustrates another embodiment of the torsional spring 266 that can be coupled to the upper jaw 200 around various pins.

Figure 9:
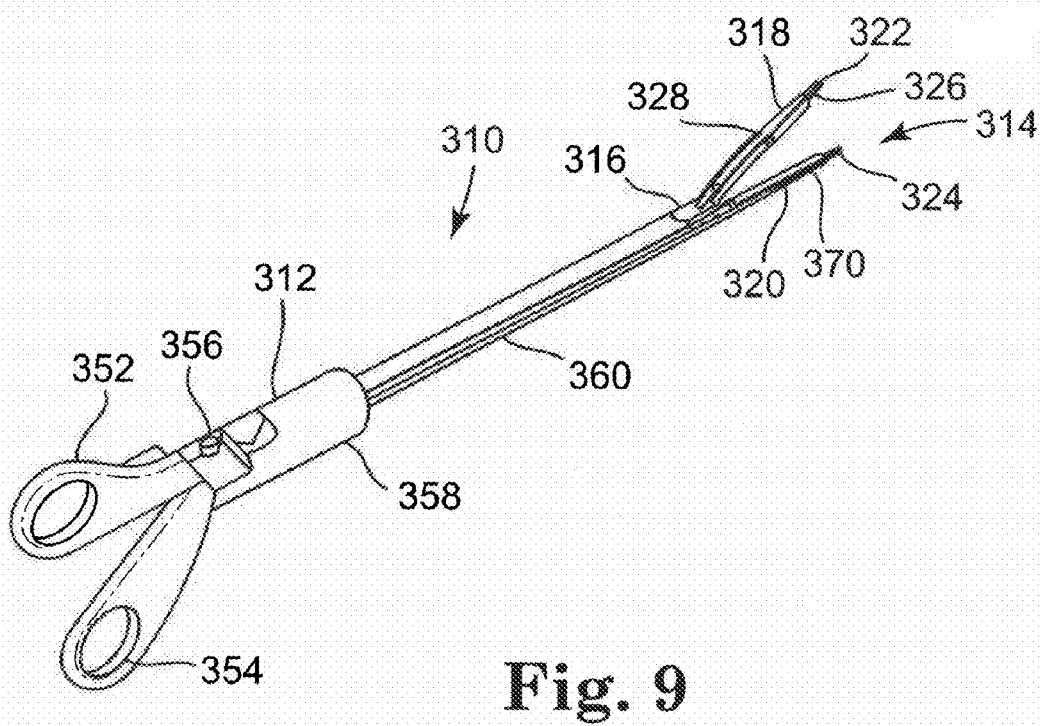
FIG. 9 is a perspective view of an ablation device according to one embodiment of the invention.
Figure 11:
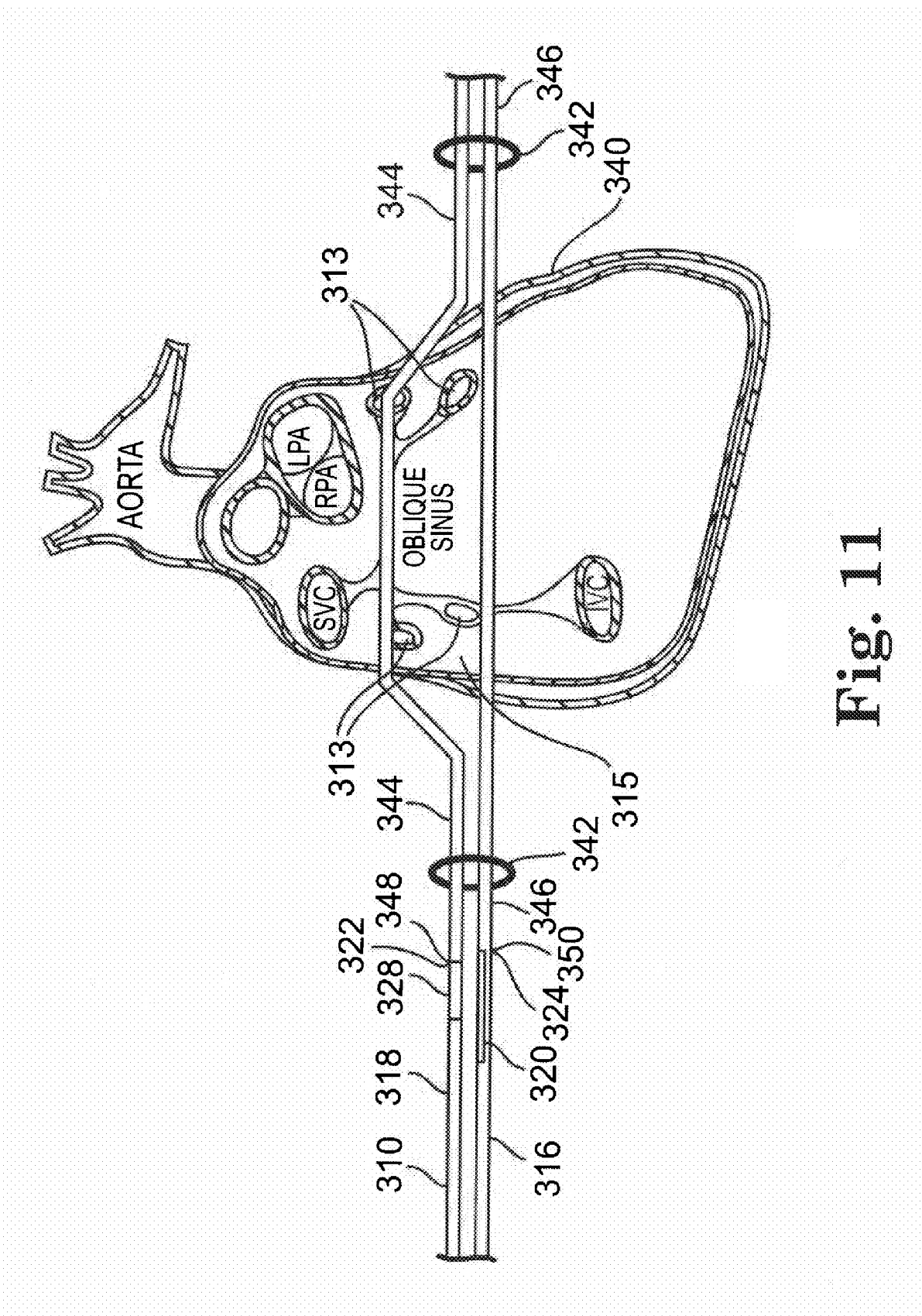
FIG. 11 is a cross-sectional view of a patient's heart with the ablation device of FIG. 9 in a closed position and coupled to catheters inserted near pulmonary veins.
Figure 12:
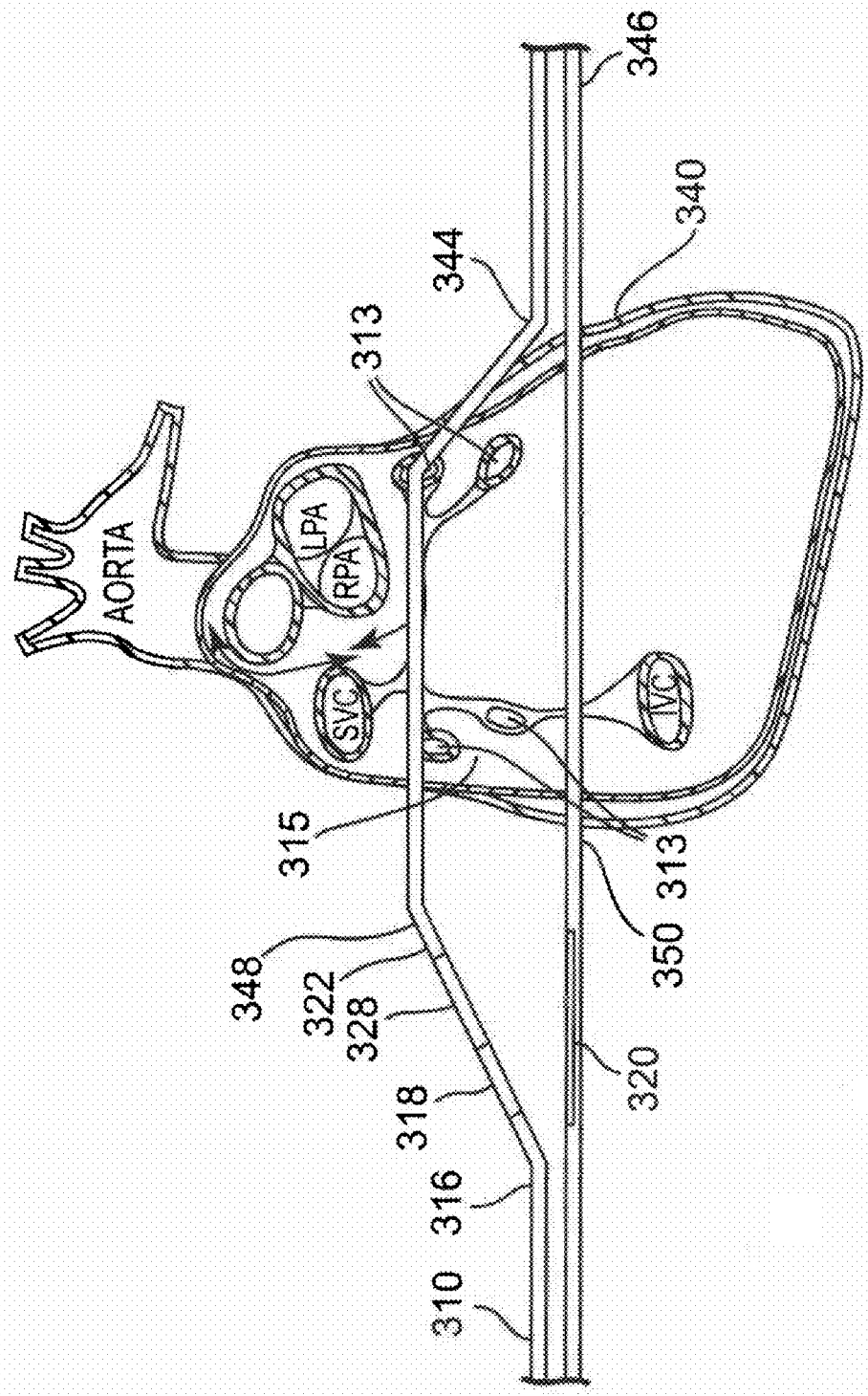
FIG. 12 is a cross-sectional view of a patient's heart with the ablation device of FIG. 1 in an open position and coupled to catheters inserted near pulmonary veins.

FIG. 9 illustrates an ablation tool 310 according to one embodiment of the invention. The ablation tool 310 can be used in conjunction with first and second catheters in an ablation system, as shown and described with respect to FIGS. 11 and 12. In some embodiments of the invention, the ablation tool 310 can be a bipolar bilateral ablation tool. The ablation tool 310 can include a handle 312, jaws 314, and a hinged connection 316. The handle 312 can be used by a surgeon to orient and close the jaws 314. The handle 312 can include a first circular portion 352 that can receive a surgeon's thumb and a second circular portion 354 that can receive one or more of a surgeon's fingers. The handle 312 can also include a hinge 356 coupled to a collar 358. The ablation tool 310 can include an elongated neck 360. The collar 358 of the handle 312 can be coupled to the elongated neck 360. The elongated neck 360 can have a length sufficient to reach target tissue 315 within a patient's heart from an incision 342 (as shown in FIGS. 11 and 12).

Figure 10:
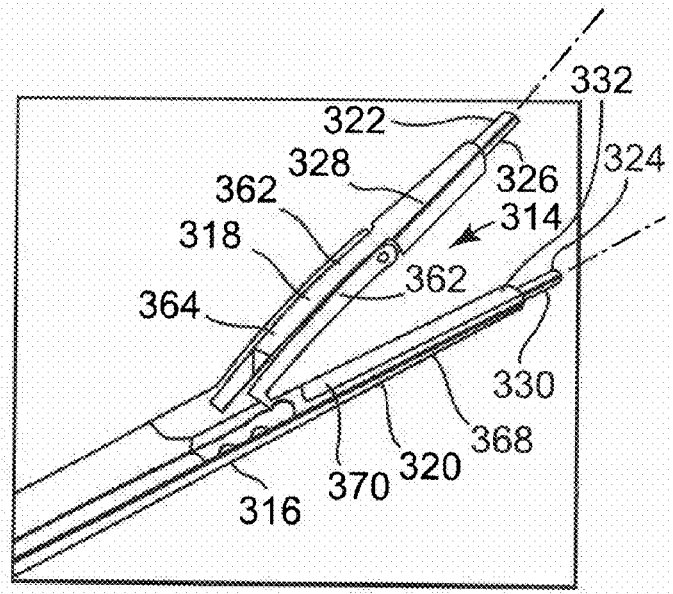
FIG. 10 is a perspective view of a distal end of the ablation device of FIG. 9.

The jaws 314 can include an upper jaw 318 and a lower jaw 320. The upper jaw 318 and the lower jaw 320 can be coupled to the hinged connection 316. The upper jaw 318 can include a first cannula connection 322, a body portion 328, lateral supports 362, and a central support 364. The lateral supports 362 can be movably coupled to the hinged connection 316. The central support 364 can be movably coupled to the lateral supports 362. The central support 364 can be rigidly coupled or integral with the body 328. The first cannula connection 322 can include a nipple 326 and can be rigidly coupled or integral with the central support 364. As shown in FIG. 10, the nipple 326 of the first cannula connection 322 can extend axially from and be aligned with the body portion 328 of the upper jaw 318. The upper jaw 318 can also include one or more upper electrodes (not shown). The one or more upper electrodes can be coupled to one or more of the body 328, the lateral supports 362, and the central support 364.

The lower jaw 320 can include a second cannula connection 324 and a body portion 368. The second cannula connection 324 can include a nipple 330 on a distal end 332 of the lower jaw 320. The nipple 330 can be aligned axially with the body portion 368 of the lower jaw 320. The lower jaw 320 can also include one or more electrodes 370 coupled to the body portion 368.

The first cannula connection 322 and the second cannula connection 324 can include any suitable connector or fastener that can mate with any suitable connector or fastener on the first and second catheters 344, 346. For example, the first and second cannula connections 322, 324 can include any suitable type of male protrusions or female recesses that can mate with corresponding female recesses and male protrusions, respectively, on the first and second catheters 344, 346. For example, press-fit connections, threaded connections, clasps, pins, clamps, sheaths, collars, or any combination thereof, can be used to connect the jaws 314 to the first and second catheters 344, 346.

In some embodiments, the first cannula connection 322 and the second cannula connection 324 can be combined in a single nipple (not shown) that can be bifurcated across both the upper jaw 318 and the lower jaw 320.

In some embodiments, the ablation tool 310 can include one or more electrodes on the upper jaw 318 and one or more electrodes 370 on the lower jaw 320 for a bipolar bilateral ablation device. The ablation tool 310 can use the hinged connection 316 to balance contact across the target tissue 315 between the jaws 314. In other embodiments, the ablation tool can include one or more electrodes on only the upper jaw 318 or the lower jaw 320 for a monopolar unilateral ablation device.

FIG. 11 illustrates the nipple 326 of the upper jaw 318 coupled to a first catheter 344 and the nipple 330 of the lower jaw 320 coupled to a second catheter 346. The first catheter 344 can be fed through a cavity 340 of the patient and out the incision 342 (e.g., in the patient's side). The first catheter 344 can be positioned along a first path in order to bring the upper jaw 18 into engagement with the target tissue 315. The second catheter 346 can be fed along a second path on an opposite side of the target tissue 315. The second catheter 346 can be positioned along the second path in order to bring the lower jaw 320 into engagement with the target tissue 315.

According to one method of the invention, as shown in FIGS. 11 and 12, the first catheter 344 and the second catheter 346 can be directed through the incision 342 into a patient's cavity until their central portions are adjacent the target tissue 315. The distal portions of the first catheter 344 and the second catheter 346 can then be directed onward and out of the patient's body cavity. The first catheter 344 can include a first proximal end 348 and the second catheter 346 can include a second proximal end 350. The first and second proximal ends 348, 350 can be in position to extend from the incision 342 before the ablation tool 310 is coupled to the first and second catheters 344, 346. The first and second proximal ends 348, 350 can be connected to the upper and lower jaws 318, 320 of the ablation tool 310. The first and second catheters 344, 346 can be pulled back into and through the patient's cavity in order to pull the ablation device 310 into the patient's cavity. The first and second catheters 344, 346 protect the patient's tissue during the insertion of the ablation tool 310 into the patient's cavity and provide a predefined path for the insertion. More specifically, the first and second catheters 344, 346 can protect the patient's tissue from being poked or dissected by the jaws 314 of the ablation tool 310 during insertion of the ablation tool 310 into the patient's cavity. The first and second catheters 344, 346 can also guide the jaws 314 of the ablation tool 310 until the jaws 314 are adjacent the target tissue 315. Ablation energy (e.g., radio frequency energy, thermal energy, cryogenic energy, microwave energy, etc.) can be provided to the one or more electrodes 370 coupled to the upper jaw 318 and/or the lower jaw 320.

After a first ablation is complete, the ablation tool 310 can be retracted from a first side of the patient's heart and then inserted along the opposite ends of the first and second catheters 344, 346 in order to ablate a second side of the patient's heart along the pulmonary veins or other target tissue 315.

Figure 13:
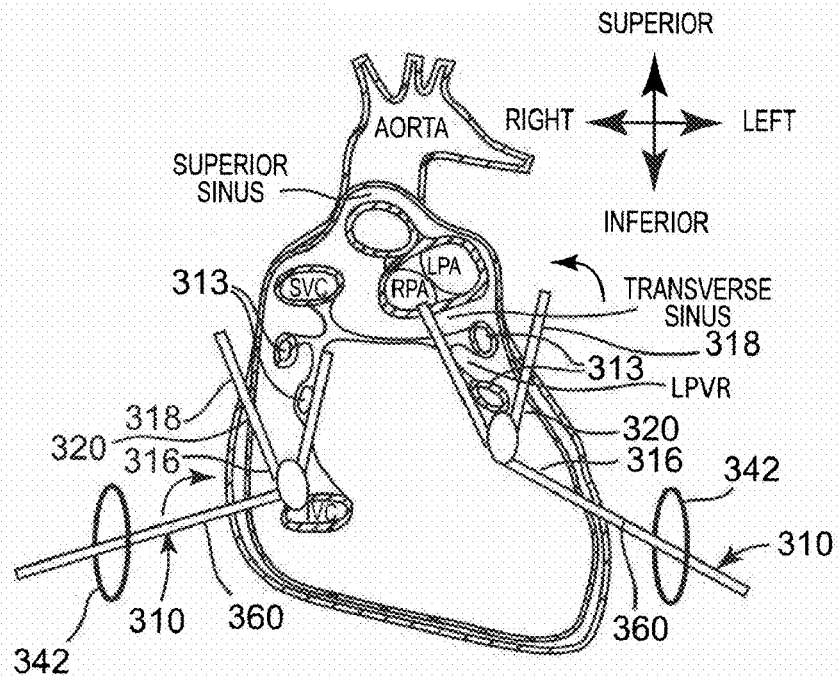
FIG. 13 is a schematic illustration of two ablation devices inserted adjacent pulmonary veins in a patient's heart.
Figure 14:
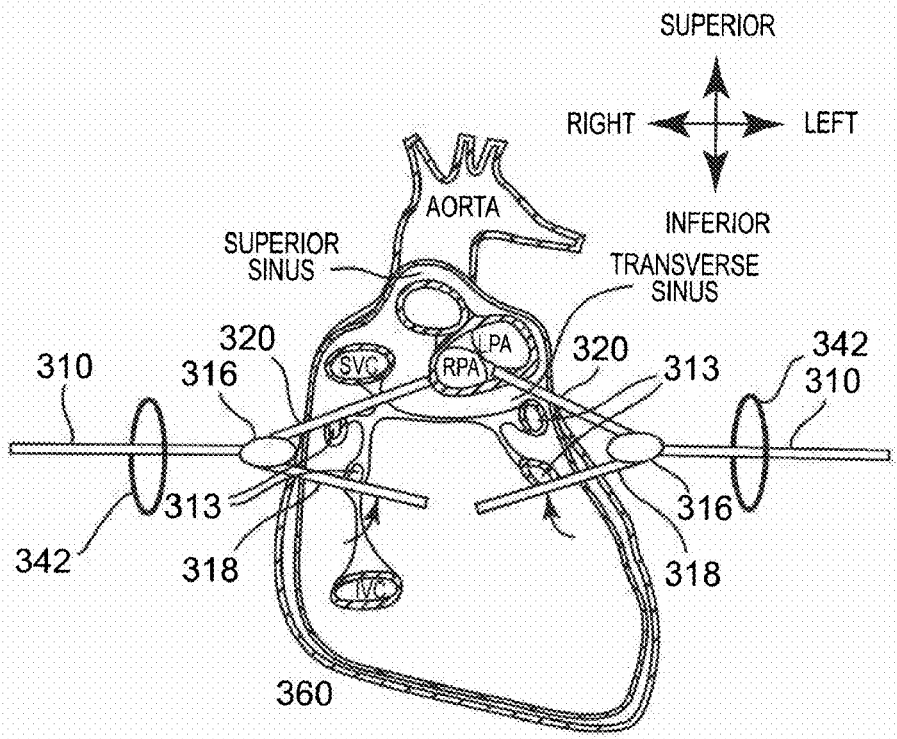
FIG. 14 is another schematic illustration of two ablation devices inserted adjacent pulmonary veins in a patient's heart.

FIGS. 13 and 14 illustrate multiple ablations and approaches that can be achieved using one or more ablation tools 310. As shown in FIGS. 13 and 14, one ablation tool 310 can be positioned to ablate tissue adjacent the right pulmonary veins, and another ablation tool 310 can be positioned to ablate tissue adjacent the left pulmonary veins. As shown in FIG. 13, the neck 360 of the ablation tool 310 can be positioned through a sixth intercostal incision and can be positioned at approximately a right angle with respect to the jaws 314. As shown in FIG. 14, the neck 360 of the ablation tool 310 can be positioned through a third intercostal incision and can be positioned along substantially the same axis as the jaws 314.

Various additional features and advantages of the invention are set forth in the following claims.

The invention claimed is:

1. An ablation device for ablating target tissue adjacent pulmonary veins of a patient, the ablation device comprising:
   a hinge including a cam assembly, the cam assembly including at least one rider and at least one finger;
   a moving arm coupled to the hinge, the moving arm including a cam surface that engages the at least one rider;
   a floating jaw coupled to the moving arm, the at least one finger engaging the floating jaw to hold the floating jaw in a first position with respect to the moving arm as the floating jaw is moved from an open position partially toward a closed position, the floating jaw including a first electrode that receives ablation energy; and
   a lower jaw coupled to the hinge, the lower jaw including a channel that receives the at least one finger, the channel allowing the floating jaw to move to a second position that is reoriented with respect to the moving arm after partial closing of the floating jaw from an open position toward a closed position, the lower jaw including a second electrode that receives ablation energy.

2. The ablation device of claim 1 wherein the cam assembly includes two riders and two fingers.

3. The ablation device of claim 1 wherein the floating jaw swivels between the first position and the second position.

4. The ablation device of claim 1 wherein the first electrode and the second electrode receive ablation energy including at least one of radio frequency energy, thermal energy, cryogenic energy, and microwave energy.

5. The ablation device of claim 1 and further comprising a neck coupled to the hinge, a collar coupled to the neck, a hinge assembly coupled to the collar, a thumb ring coupled to the hinge assembly, and a trigger coupled to the hinge assembly.

6. The ablation device of claim 5 and further comprising a cable coupled between the trigger and at least one of the moving arm and the floating jaw.

* * * * *